(12) United States Patent
Bregman-Amitai et al.

(10) Patent No.: US 10,327,725 B2
(45) Date of Patent: Jun. 25, 2019

(54) SYSTEMS AND METHODS FOR EMULATING DEXA SCORES BASED ON CT IMAGES

(71) Applicant: Zebra Medical Vision Ltd., Shefayim (IL)

(72) Inventors: Orna Bregman-Amitai, Tel-Aviv (IL); Eldad Elnekave, Tel-Aviv (IL)

(73) Assignee: Zebra Medical Vision Ltd., Shefayim (IL)

( * ) Notice: Subject to any disclaimer, the term of this patent is extended or adjusted under 35 U.S.C. 154(b) by 0 days.

(21) Appl. No.: 16/155,938

(22) Filed: Oct. 10, 2018

(65) Prior Publication Data

US 2019/0046146 A1    Feb. 14, 2019

Related U.S. Application Data

(63) Continuation of application No. 15/964,086, filed on Apr. 27, 2018, now Pat. No. 10,111,637, which is a
(Continued)

(51) Int. Cl.
*A61B 6/00* (2006.01)
*A61B 6/03* (2006.01)
*G06T 7/00* (2017.01)

(52) U.S. Cl.
CPC ............ *A61B 6/5217* (2013.01); *A61B 6/032* (2013.01); *A61B 6/481* (2013.01); *A61B 6/482* (2013.01);
(Continued)

(58) Field of Classification Search
CPC ....... A61B 6/5217; A61B 6/032; A61B 6/481; A61B 6/482; A61B 6/505; A61B 6/5252; G06T 7/001
See application file for complete search history.

(56) References Cited

U.S. PATENT DOCUMENTS 8,818,484 B2    8/2014   Liew et al.
8,831,305 B2    9/2014   Zhang et al.
(Continued)

FOREIGN PATENT DOCUMENTS

WO    WO 2016/013004    1/2016
WO    WO 2016/013005    1/2016

OTHER PUBLICATIONS

International Preliminary Report on Patentability dated Feb. 2, 2017 From the International Bureau of WIPO Re. Application No. PCT/IL2015/050743. (6 Pages).
(Continued)

*Primary Examiner* — Mia M Thomas

(57) ABSTRACT

Computerized methods and systems for estimating a dual-energy X-ray absorptiometry (DEXA) score from CT imaging data by receiving imaging data of a computed tomography (CT) scan of a body of a patient containing at least a bone portion, segmenting the bone portion from the imaging data, computing at least one grade based on pixel associated values from the bone portion, and correlating the at least one grade with at least one score representing a relation to bone density values in a population obtained based on a DEXA scan. The grade is computed from a calculation of sub-grades performed for each one or a set of pixels having at least one of a common medial-lateral axial coordinate and a common cranial-caudal axial coordinate along a dorsal-ventral axis of a volume representation of the imaging data.

24 Claims, 24 Drawing Sheets

Related U.S. Application Data continuation of application No. 14/726,813, filed on Jun. 1, 2015, now Pat. No. 10,039,513.

(60) Provisional application No. 62/026,730, filed on Jul. 21, 2014.

(52) U.S. Cl.
CPC ............ *A61B 6/505* (2013.01); *A61B 6/5252* (2013.01); *G06T 7/0012* (2013.01); *G06T 2207/10081* (2013.01); *G06T 2207/20081* (2013.01); *G06T 2207/30012* (2013.01)

(56) References Cited

U.S. PATENT DOCUMENTS

| | | | |
|---|---|---|---|
| 8,855,389 B1 | 10/2014 | Hoffmann et al. | |
| 8,913,818 B2 | 12/2014 | Lang et al. | |
| 8,923,594 B2* | 12/2014 | Wehnes | G06T 7/0012 |
| | | | 382/132 |
| 8,965,075 B2 | 2/2015 | Arnaud et al. | |
| 9,153,021 B2 | 10/2015 | Wilson | |
| 9,155,501 B2 | 10/2015 | Lang et al. | |
| 9,211,103 B2 | 12/2015 | Kraus et al. | |
| 9,267,955 B2 | 2/2016 | Lang et al. | |
| 9,274,037 B2 | 3/2016 | Huwer et al. | |
| 9,532,750 B2 | 1/2017 | Dzyubak et al. | |
| 9,589,204 B2 | 3/2017 | Gremse et al. | |
| 9,775,577 B2 | 10/2017 | Chang et al. | |
| 9,848,818 B1 | 12/2017 | Kopperdahl et al. | |
| 9,936,934 B2 | 4/2018 | Kopperdahl et al. | |
| 9,940,711 B2* | 4/2018 | Bregman-Amitai | G06T 7/0012 |
| 10,039,513 B2* | 8/2018 | Bregman-Amitai | G06T 7/0012 |
| 10,111,637 B2* | 10/2018 | Bregman-Amitai | G06T 7/0012 |
| 2002/0009215 A1 | 1/2002 | Armato, III et al. | |
| 2002/0075997 A1 | 6/2002 | Unger et al. | |
| 2002/0181651 A1 | 12/2002 | Shepherd et al. | |
| 2002/0191823 A1 | 12/2002 | Wehrli et al. | |
| 2004/0101104 A1 | 5/2004 | Avinash et al. | |
| 2004/0120922 A1 | 6/2004 | Burke | |
| 2004/0171931 A1 | 9/2004 | Barth et al. | |
| 2006/0062442 A1 | 3/2006 | Arnaud et al. | |
| 2006/0106459 A1 | 5/2006 | Truckai et al. | |
| 2007/0223799 A1 | 9/2007 | Weiss | |
| 2008/0025584 A1 | 1/2008 | Kunz et al. | |
| 2008/0082002 A1 | 4/2008 | Wilson et al. | |
| 2008/0216845 A1 | 9/2008 | De Bruijne et al. | |
| 2009/0093852 A1 | 4/2009 | Hynes | |
| 2009/0297012 A1 | 12/2009 | Brett et al. | |
| 2010/0177946 A1 | 7/2010 | De Bruijne et al. | |
| 2011/0036360 A1 | 2/2011 | Lang et al. | |
| 2011/0142307 A1 | 6/2011 | Ghosh et al. | |
| 2011/0158494 A1 | 6/2011 | Bar-Shalev et al. | |
| 2011/0208033 A1 | 8/2011 | Nicolella et al. | |
| 2011/0257507 A1 | 10/2011 | Gregory et al. | |
| 2011/0317898 A1 | 12/2011 | Shi et al. | |
| 2012/0004594 A1 | 1/2012 | Schulz et al. | |
| 2012/0143090 A1 | 6/2012 | Hay et al. | |
| 2013/0004043 A1 | 1/2013 | Ross et al. | |
| 2013/0077840 A1 | 3/2013 | Blumfield et al. | |
| 2013/0137988 A1 | 5/2013 | Bregman-Amitai et al. | |
| 2013/0259190 A1 | 10/2013 | Walls et al. | |
| 2013/0301794 A1 | 11/2013 | Grader et al. | |
| 2014/0072571 A1 | 3/2014 | Urdea et al. | |
| 2014/0177788 A1 | 6/2014 | Stevens et al. | |
| 2014/0275705 A1 | 9/2014 | Virshup et al. | |
| 2014/0336503 A1 | 11/2014 | Kilbourn et al. | |
| 2014/0371570 A1 | 12/2014 | Davis et al. | |
| 2015/0110373 A1 | 4/2015 | Shaham et al. | |
| 2015/0164454 A1 | 6/2015 | Grant et al. | |
| 2015/0173703 A1 | 6/2015 | Siewerdsen et al. | |
| 2015/0196264 A1 | 7/2015 | Luo et al. | |
| 2015/0348259 A1 | 12/2015 | Souza et al. | |
| 2016/0015347 A1 | 1/2016 | Bregman-Amitai et al. | |
| 2016/0045733 A1 | 2/2016 | McGeoch et al. | |
| 2016/0113612 A1 | 4/2016 | Sedlmair et al. | |
| 2016/0183355 A1 | 6/2016 | Lou et al. | |
| 2016/0302748 A1 | 10/2016 | Chang et al. | |
| 2016/0338649 A1 | 11/2016 | Branch et al. | |
| 2017/0148156 A1 | 5/2017 | Bregman-Amitai et al. | |
| 2018/0075628 A1* | 3/2018 | Teare | A61B 6/5217 |
| 2018/0116584 A1 | 5/2018 | Kopperdahl et al. | |
| 2018/0242943 A1 | 8/2018 | Bregman-Amitai et al. | |
| 2018/0333140 A1* | 11/2018 | Wodlinger | A61B 8/085 |

OTHER PUBLICATIONS

International Preliminary Report on Patentability dated Feb. 2, 2017 From the International Bureau of WIPO Re. Application No. PCT/IL2015/050744. (9 Pages).

International Search Report and the Written Opinion dated May 17, 2016 From the International Searching Authority Re. Application No. PCT/IL2015/050744.

International Search Report and the Written Opinion dated Dec. 22, 2015 From the International Searching Authority Re. Application No. PCT/IL2015/050743.

Invitation to Pay Additional Fees dated Dec. 4, 2015 From the International Searching Authority Re. Application No. PCT/IL2015/050744.

Official Action dated Jun. 2, 2017 from the US Patent and Trademark Office Re. U.S. Appl. No. 14/726,813. (36 pages).

AOSpine "Spinal Fractures Classification System." AOSpine Knowledge Forum, 2016, 72 pages.

Carberry et al. "Unreported Vertebral Body Compression Fractures at Abdominal Multidetector CT", Radiology, 268(1): 120-126, Jul. 2013.

Cummings et al. "Epidemiology and Outcomes of Osteoporotic Fractures", The Lancet, 359: 1761-1767, May 18, 2002.

Davidson et al. "Protocol for Measurement of Liver Fat by Computed Tomography," Journal of Applied Physiology 100: 864-868, 2006.

Engelke et al. "Clinical Use of Quantitative Computed Tomography and Peripheral Quantitative Computed Tomography in the Management of Osteoporosis in Adults: The 2007 ISCD Official Positions", Journal of Clinical Densitometry: Assessment of Skeletal Health, 11(1): 123-162, Jan.-Mar. 2008. Abstract, p. 124, col. 1, p. 130, col. 2, p. 135, col. 2, p. 142, col. 2, p. 151, col. 2.

Harrigan et al. "Predicting Bone Mechanical Properties of Cancellous Bone from DXA, MRI, and Fractal Dimensional Measurements." Final Report, TMC-NASA Collaborative Research Project, 1997, 6 pages.

Kanis "Diagnosis of Osteoporosis and Assessment of Fracture Risk", The Lancet, 359: 1929-1936, Jun. 1, 2002.

Kanis et al. "European Guidance for the Diagnosis and Management of Osteoporosis in Postmenopausal Woman", Osteoporosis International, 24: 23-57, 2013.

Keenan et al. "Comparison of Bone Density Measurement Techniques: DXA and Archimedes' Principle." Journal of Bone and Mineral Research 12(11): 1903-1907, 1997.

Langer "A Flexible Database Architecture for Mining DICOM Objects: The DICOM Data Warehouse", Journal of Digital Imaging, 25: 206-212, 2012.

Link "Osteoporosis Imaging: State of the Art and Advanced Imaging", Radiology, 263(1): 3-17, Apr. 2012.

Majumdar et al. "Conventional Computed Tomography Imaging and Bone Mineral Density: Opportunistic Screening or 'Incidentaloposis'?", Annals of Internal Medicine, 158: 630-631, 2013.

Nguyen et al. "Osteoporosis: Underrated, Underdiagnosed and Undertreated", The Medical Journal of Australia, MJA, 1805/Suppl. ): S18-S22, Mar. 1, 2004.

Pickhardt et al. "Opportunistic Screening for Osteoporosis Using Abdominal Computed Tomography Scans Obtained for Othe Indications", Annals of Internal Medicine, 158: 588-595, 2013.

(56) References Cited

OTHER PUBLICATIONS

Pickhardt et al. "Simultaneous Screening for Osteoporosis at CT Colonography: Bone Mineral Density Assessment Using MDCT Attenuation Techniques Compared Against the DXA Reference Standard", Journal of Bone and Mineral Research, 26(9): 2194-2203, Sep. 2011.

Rajasekaran et al. "The Value of CT and MRI in the Classification and Surgical Decision-Making Among Spine Surgeons in Thoracolumbar Spinal Injuries." European Spine Journal (Jun. 1, 2016): 1-7.

Reinhold et al. "AO Spine Injury Classification System: a Revision Proposal for the Thoracic and Lumbar Spine." European Spine Journal 22(10): 2184-2201, 2013.

Schwaiger et al. "Bone Mineral Density Values Derived From Routine Lumbar Spine Multidetector Row CT Predict Osteoporotic Vertebral Fractures and Screw Loosening", American Journal of Neuroradiology, AJNR, p. 1-6, Mar. 13, 2014.

Siris et al. "Identification and Fracture Outcomes of Undiagnosed Low Bone Mineral Density in Postmenopausal Women", Journal of the American Medical Association, JAMA, 286(22): 2815-2822, Dec. 12, 2001.

Summers et al. "Feasibility of Simultaneous CT Colonography and Fully-Automated Bone Mineral Densitometry in a Single Examination", Journal of Computer Assisted Tomography, 35(2): 212-216, Mar.-Apr. 2011.

Wahner "The Evaluation of Osteoporosis: Dual Energy X-ray Absorptiometry in Clinical Practice," Book Review, European Journal of Radiology 19: 151-153, 1995.

Williams et al. "Under-Reporting of Osteoporotic Vertebral Fractures on Computed Tomography", European Journal of Radiology, 69: 179-183, 2009.

* cited by examiner

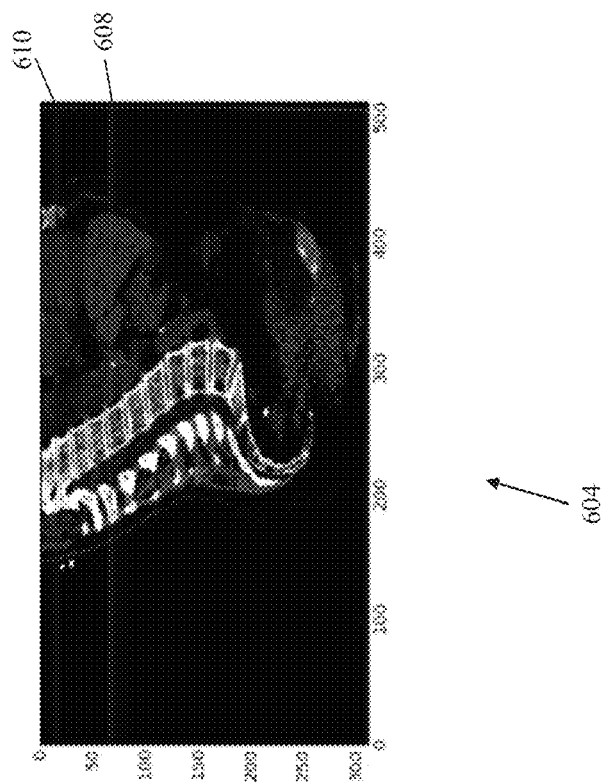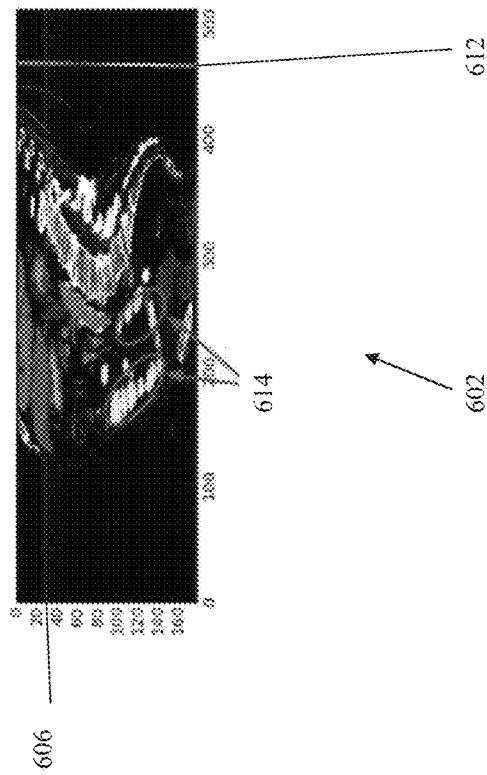
FIG. 6

FIG. 18

| | err<5% | err<6% | err<7% | err<8% | err<9% | err<10% | err<12% | err<15% |
|---|---|---|---|---|---|---|---|---|
| | | | | Lumbar T-Score | | | | |
| accuracy fraction | 0.32 | 0.39 | 0.44 | 0.50 | 0.55 | 0.61 | 0.70 | 0.80 |
| | | | | Total T-Score | | | | |
| accuracy fraction | 0.38 | 0.44 | 0.51 | 0.57 | 0.62 | 0.67 | 0.75 | 0.86 |

| calculated T-Score range | True category fraction | | |
|---|---|---|---|
| | Osteoporosis | Osteopenia | Normal |
| -6.0 : -2.5 | 0.443 | 0.409 | 0.148 |
| -2.5 : -1 | 0.369 | 0.367 | 0.263 |
| -1 : 4 | 0.186 | 0.422 | 0.392 |

Table 1902

| calculated T-Score range | True category fraction | | |
|---|---|---|---|
| | Osteoporosis | Osteopenia | Normal |
| -4.000000 - -3.500000 | 0.842 | 0.158 | 0 |
| -3.500000 - -3.000000 | 0.737 | 0.26 | 0.003 |
| -3.000000 - -2.500000 | 0.58 | 0.379 | 0.041 |
| -2.500000 - -2.000000 | 0.407 | 0.471 | 0.122 |
| -2.000000 - -1.500000 | 0.248 | 0.503 | 0.25 |
| -1.500000 - -1.000000 | 0.137 | 0.482 | 0.381 |
| -1.000000 - -0.500000 | 0.085 | 0.351 | 0.564 |
| -0.500000 - 0.000000 | 0.025 | 0.245 | 0.73 |
| 0.000000 - 0.500000 | 0.021 | 0.064 | 0.915 |
| 0.500000 - 1.000000 | 0 | 0.02 | 0.98 |
| 1.000000 - 1.500000 | 0 | 0 | 1 |

Table 1904

FIG. 19

SYSTEMS AND METHODS FOR EMULATING DEXA SCORES BASED ON CT IMAGES

RELATED APPLICATIONS

This application is a continuation of U.S. patent application Ser. No. 15/964,086 filed on Apr. 27, 2018, which is a continuation of U.S. patent application Ser. No. 14/726,813 filed on Jun. 1, 2015, now U.S. Pat. No. 10,039,513, which claims the benefit of priority under 35 USC § 119(e) of U.S. Provisional Patent Application No. 62/026,730 filed on Jul. 21, 2014, the contents of which are incorporated herein by reference in their entirety.

FIELD AND BACKGROUND OF THE INVENTION

The present invention, in some embodiments thereof, relates to systems and methods for diagnosing an osteoporotic patient and, more specifically, but not exclusively, to systems and methods for estimation a score representing a relation to bone density values in a healthy young population or a demographically matched population.

Osteoporosis remains a prevalent, burdensome and markedly under-diagnosed condition. DXA (Duel-Energy X-ray Absorptiometry) remains the diagnostic standard for assessing bone mineral density (BMD). However, fewer than 50% of eligible Medicare recipients undergo bone mineral density screening. Underutilization of DXA together with suboptimal test predictive indices may account for the finding that an estimated 80% of patients who experience osteoporotic fractures have either not undergone prior screening or received appropriate treatment. It is important to note that early diagnosis and prophylactic treatment can reduce the risk of osteoporotic fractures by 30-70%.

SUMMARY OF THE INVENTION

According to an aspect of some embodiments of the present invention there is provided a computerized method for estimating a DEXA score from CT imaging data, comprising: receiving imaging data of a computed tomography (CT) scan of a body of a patient containing at least a bone portion; segmenting the bone portion from the imaging data; computing at least one grade based on pixel associated values from the bone portion; and correlating the at least one grade with at least one score representing a relation to bone density values in a population obtained based on a dual-energy X-ray absorptiometry (DEXA) scan; wherein the grade is computed from a calculation of sub-grades performed for each one or a set of pixels having at least one of a common medial-lateral axial coordinate and a common cranial-caudal axial coordinate along a dorsal-ventral axis of a volume representation of the imaging data.

Optionally, the grade is computed from sub-grades calculated for each of the bone portions comprising vertebral bodies of at least one of L1, L2, L3, and L4 vertebrae.

Optionally, the grade is computed by calculation of an average pixel associated value for pixel associated values above a predefined threshold selected from about 150-300 Hounsfield Units (HU), the pixels having a common x,z-coordinate, and along a y-axis of a volume representation of the imaging data. Optionally, the grade is computed based on at least one member of the group consisting of: minimal grade of sub-grades computed for each vertebra of a plurality of vertebrae, average grade of sub-grades computed for a plurality of vertebrae, average grade of sub-grades computed for a plurality of defined sections each including portions of a plurality of vertebrae, and grade computation for a single predefined vertebra.

Optionally, the method further comprises inverting pixel coordinates of the imaging data according to a predefined common patient position when the predefined common patient position is different than the identified position of the patient.

Optionally, the segmented bone portion excludes contrast agent having pixel associated values representing bone.

Optionally, correlating comprises at least one of: selecting a grade from a plurality of sub-grades to correlate with a single score, and correlating each of a plurality of sub-grades with a respective sub-score and selecting the lowest sub-score as the score.

Optionally, the score is a DEXA T-score. Optionally, the T-score is a member selected from the group consisting of: T-score per vertebra, lumbar T-score, and total T-score.

Optionally, the correlating is performed to one of a plurality of classification groups of the score. Optionally, the classification groups consist of: greater than one standard deviation below the mean (−1), between one (−1) and two and a half (−2.5) standard deviations below the mean, and less than two and a half standard deviations below the mean (−2.5). Alternatively or additionally, the classification groups are bins each representing half a standard deviation. Alternatively or additionally, the classification groups are diagnostic classification groups consist of: normal, and abnormal. Alternatively or additionally, the classification groups are diagnostic classification groups consist of: normal, osteoporotic, and osteoporosis. Alternatively or additionally, the classification groups are automatically generated based on a predefined probability threshold.

Optionally, the score is a DEXA Z-score.

Optionally, the correlating is performed by statistical classifier trained on a dataset including, for each patient, a DEXA score calculated from a DEXA scan, and a CT scan generating an imaging dataset used for calculating the grade.

Optionally, segmenting the bone portion from the imaging data comprises: identifying a z-coordinate limitation of a region of interest (Z-ROI) including the L1-L4 lumbar vertebrae from the imaging data, and per z-coordinate slice identifying an x-coordinate limitation of the respective vertebrae (X-ROI). Optionally, the method further comprises masking organs affected by a contrast agent within the ROI.

Optionally, the method further comprises counting a number of pixels representing lung tissue for each axial slice of a volume generated from the imaging data; designating z-coordinates according to the largest identified decrease in the number of lung pixels between sequential axial slices, wherein the designated z-coordinates represent an approximate location of the T12 vertebrae; and wherein segmenting comprises segmenting at least one of the L1-L4 vertebrae according to the designated z-coordinates.

Optionally, the method further comprises analyzing a sagittal section of the imaging data to identify a border of a back of the patient; and wherein segmenting comprises segmenting at least one of the L1-L4 vertebrae according to the identified border of the back of the patient.

Optionally, the analyzing is performed using an image window size selected to exclude ribs to identify a first of the border, and further comprising: analyzing the sagittal section of the image data using a second window size selected to include ribs to identify a second border of the back of the patient; comparing proximity of the coordinates of the first border to the second border; identifying a position of the patient relative to a scan table according to the proximity of the coordinates; and inverting pixel coordinates of the imaging data according to a predefined common patient position when the predefined common patient position is different than the identified position of the patient. Optionally, segmenting comprises generating a binary map of a region large enough to include vertebra and connected rib portions while excluding other nearby tissues from the identified border according to a first pixel associated value assigned to pixels in the region above a pixel threshold, and a second pixel associated value assigned to pixels in the region below the pixel threshold. Optionally, the binary map is generated in a coronal view.

Optionally, the method further comprises selecting a largest connected component of the imaging data that crosses a z-coordinate defining an end of a lung of the patient; and identifying a central line of the largest connected component; identifying side boundaries of the largest connected component; wherein the largest connected component is a binary map having values representing bone or other; and wherein segmenting comprises segmenting according to the largest connected component by identifying the L1-L4 on the imaging data by correlating the largest connected components to the imaging data to identify a T12 vertebrate when a lowest rib is connected and an L5 vertebrae according to a location where the width of the largest connected component increases representing a hip of the patient.

Optionally, segmenting is performed on a sagittal section defined within a region of the imaging data designated below an identified lower limit of a lung of the patient and a border of a back of the patient. Optionally, the region is further defined by a border between a vertebral column of the patient and other organs in near proximity, and a border between a spinal cord and the vertebral column, such that the identified vertebral column includes vertebral bodies and excludes vertebral pedicles and processes.

Optionally, segmenting comprises transforming identified vertebral bodies to a vertical alignment according to calculated gradients between each vertebral body and the spinal column, identifying borders of at least one of the L1, L2, L3, and L4 vertebral bodies on the vertical alignment according to identified vertical lines, and marking the identified vertebral bodies on the imaging data according to a mapping from the vertical alignment to the imaging data.

Optionally, the bone portion includes at least one vertebra selected from at least one of: at least one cervical vertebra and at least one thoracic vertebra.

Optionally, the CT scan imaging data is inadequate for estimating a bone mineral density (BMD) measurement of the bone portion.

Optionally, the CT scan imaging data is inadequate for performing a quantitative computed tomography scan (QCT) for measurement of BMD.

Optionally, the received CT scan has been ordered for diagnosis of non-osteoporosis medical conditions based on non-osteoporosis related signs and/or symptoms.

Optionally, the CT scan is performed with settings selected for imaging of non-osteoporosis related pathology.

Optionally, the CT scan is ordered for a conventional clinical indication including at least one member of a group consisting of: low dose CT scan of the chest to screen for lung cancer, CT scan to screen for colon cancer, standard non-contrast CT scan of the chest, IV contrast CT scan of the chest, standard non-contrast CT scan of the abdomen, IV contrast CT scan of the abdomen, oral contrast CT scan of the abdomen, pelvic CT scan.

Optionally, segmenting comprises identifying an approximate region of interest (ROI) including an un-segmented component of the bone portion and another connected bone other than the bone portion.

Optionally, segmenting comprises: identifying insufficient amount of contrast agent to affect the grade calculation; and excluding a scanning bed from the imaging data by identifying a single component of the patient's body, and selecting the single component.

According to an aspect of some embodiments of the present invention there is provided a system for estimating a DEXA score from CT imaging data, comprising: an imaging interface for receiving imaging data of a computed tomography (CT) scan of a body of a patient containing at least a bone portion; an output interface for communicating with a user interface; a program store storing code; and a processor coupled to the imaging interface, the output interface, and the program store for implementing the stored code, the code comprising: code to receive the imaging data; code to segment the bone portion from the imaging data; code to compute at least one grade based on pixel associated values from the bone portion; code to correlate the at least one grade with at least one score representing a relation to bone density values in a population obtained based on a DEXA scan; and code to provide the correlated score to the output unit for presentation on the user interface; wherein the grade is computed from a calculation of sub-grades performed for each one or a set of pixels having at least one of a common medial-lateral axial coordinate and a common cranial-caudal axial coordinate along a dorsal-ventral axis of a volume representation of the imaging data.

Optionally, the CT scan includes at least one of a chest and an abdomen of the patient.

Optionally, the system further comprises code to generate a presentation including the segmented bone portion, and for each section of the segmented bone portion, the respective computed at least one grade, a correlated T-score, and a correlated Z-score. Optionally, the presentation further includes at least one of a sagittal and a coronal sub-region of the imaging data including the bone portion. Optionally, the at least one of the sagittal and coronal sub-region includes at least one of: a line representing a lower limit of a lung of the patient, and a line representing a hip.

According to an aspect of some embodiments of the present invention there is provided a computerized method of creating a trained statistical classifier for use in a process to estimate a DEXA score from CT imaging data, comprising: receiving a corpus of training image files, the training image files comprising imaging data of a CT scan of a body image of at least one patient containing at least one bone portion; segmenting the bone portion from the imaging data of each respective CT scan; computing at least one grade based on pixel associated values from the bone portion for each respective CT scan; receiving, for each of the at least one patient, at least one score representing a relation to bone density values in a population, the at least one score calculated based on a DEXA scan; training a statistical classifier based on the computed at least one grade and associated at least one score; and providing the trained statistical classifier for use in a process to estimate a score representing a relation to bone density values in a healthy young population based on at least one grade calculated from imaging data; wherein the grade is computed from a calculation of sub-grades performed for each one or a set of pixels having at least one of a common medial-lateral axial coordinate and a common cranial-caudal axial coordinate along a dorsal-ventral axis of a volume representation of the imaging data.

Optionally, the score is at least one of: T-score and Z-score.

Optionally, the CT scan and the DEXA scan are performed within about 6 months of each other.

Optionally, the CT scans include patients in prone and supine positions.

Optionally, the method further comprises assigning weights to the at least one score calculated based on the DEXA scan according to a diagnosis category.

Optionally, training comprises training multiple specialized statistical classifiers according to at least one of a patient demographic profile and a scanning protocol.

According to an aspect of some embodiments of the present invention there is provided a computerized method for selection of a group from a database for healthcare delivery, comprising: receiving a corpus of CT image files each comprising imaging data including at least a bone portion of a body of a patient; segmenting the bone portion from each imaging data of each CT image file; computing at least one grade based on pixel associated values from the bone portion; correlating the at least one grade with at least one score representing a relation to bone density values in a population obtained based on a DEXA scan; selecting a group from the corpus according to a requirement of the score; and providing an indication of the selected group; wherein the grade is computed from a calculation of subgrades performed for each one or a set of pixels having at least one of a common medial-lateral axial coordinate and a common cranial-caudal axial coordinate along a dorsal-ventral axis of a volume representation of the imaging data.

Optionally, the correlating is performed to one of a plurality of classification groups of the score, and the requirement is a designation of one or more of the classification groups.

Optionally, the requirement is at least one of a threshold value and a range of values of a DEXA T-score or a DEXA Z-score.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 6 includes two example CT scans with marked locations where lungs end, in accordance with some embodiments of the present invention;

FIG. 18 is an example chart illustrating the error of the generated trained classifier, in accordance with some embodiments of the present invention;

FIG. 19 includes examples of tables depicting an increase in accuracy that may be achieved by selecting the categorization bins for the correlated score, in accordance with some embodiments of the present invention;

DESCRIPTION OF SPECIFIC EMBODIMENTS OF THE INVENTION

Figure 1:
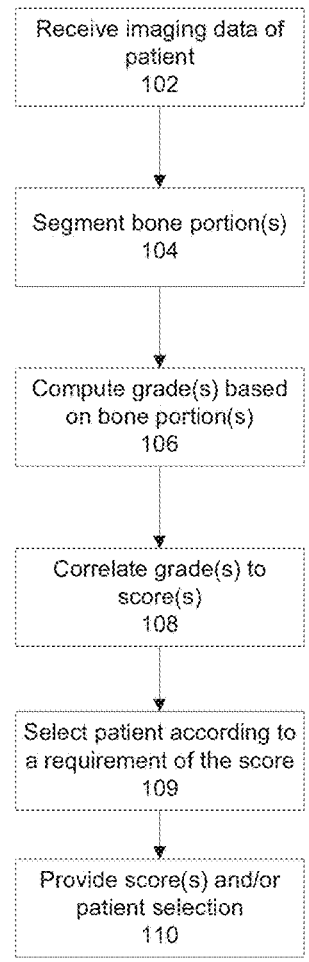
FIG. 1 is a flowchart of a method for estimating a DEXA score from CT imaging data, in accordance with some embodiments of the present invention.

The present invention, in some embodiments thereof, relates to systems and methods for diagnosing an osteoporotic patient and, more specifically, but not exclusively, to systems and methods for estimation a score representing a relation to bone density values in a healthy young population or a demographically matched population.

An aspect of some embodiments of the present invention relates to systems and/or methods (optionally code stored in a program store and implementable by a processor) for estimating a score representing a relation to bone mineral density values in a population acquired using dual-energy X-ray absorptiometry (DEXA or DXA) scanning, optionally a DEXA score, from imaging data of a patient acquired by an imaging modality (e.g., computed tomography (CT) scan). Optionally, a grade is computed from a computation of sub-grades (or the grade directly) performed for a set of pixels along a front-back direction of the patient. The set of pixels may have at least one common coordinate, for example, along a left-right direction and/or along a head-feet direction (directions relative to the patient). The computation (for the grade or sub-grade) may be, for example, the average of the set of pixels along the front-back direction, and/or the minimum value of the set of pixels. The grade may be computed based on a slice of imaging data (e.g., for pixels along a front-back dimension of the slice). Alternatively or additionally, the grade is computed based on a volume of imaging data, for example, for a set of pixels along the front-back dimension of the volume. Optionally, multiple sub-grades are calculated for each set of pixels, and the grade is calculated from the sub-grades, for example, multiple averages for multiple sets each along a different front-back dimension (e.g., parallel to each other), with the final average calculated from the multiple averages.

It is noted that the directions and/or dimensions described herein may be approximations, for example, the front-back dimension (or other dimensions and/or directions described herein) may be slightly deviated from a perfect front-back axis, for example within 10 degrees, or 30 degrees, or 45 degrees.

Optionally a grade is computed from a calculation of sub-grades performed for each one or a set of pixels having a common medial-lateral axial coordinate and/or a common cranial-caudal axial coordinate along a dorsal-ventral axis of a volume representation of the imaging data. The grade is correlated with the score. In this manner, the grade computation may consider a volume of the vertebra, which may include the vertebral body, such as the cortical and trabecular bone (instead of, for example, calculating a grade from a single CT slice including a small region of trabecular bone). Each sub-grade may be computed, for example, from at least 50%, or at least 75%, or at least 90% of the pixels in each set along the respective front-back dimension and/or axis. The grade may be computed, for example, from at least 50%, or at least 75%, or at least 90% of the pixels in the identified volume (and/or slice).

Optionally, the CT scan is performed with settings selected for imaging of non-osteoporosis related pathology. Optionally the score is a DEXA T-score (i.e., related to a healthy young population) and/or a DEXA Z-score (i.e., related to a population that is demographically similar to the patient). The systems and/or methods may use CT data performed for non-osteoporosis related pathology to estimate the DEXA score. In this manner, CT scans that are performed for clinical indications other than osteoporosis evaluation may be evaluated and scored to generate an estimate of a clinically relevant score that may serve as a screen or diagnosis for osteoporosis or osteopenia. When the CT scan is performed for an osteoporosis related pathology (e.g., evaluation of an osteoporotic fracture) the acquired CT data may be used to estimate the DEXA score, for example, instead of performing an independent DEXA scan on the patient. The patient may be spared additional doses of radiation. Optionally, the score is estimated by correlating one or more grades calculated from pixel associated data of one or more bones (optionally one or more of L1, L2, L3, and L4 lumbar vertebrae) segmented from the CT imaging data. The grades may be correlated to the corresponding score by a trained statistical classifier. The grades may be classified to one of multiple categories, optionally clinically relevant categories and/or clinically accepted diagnostic categories, for example, categories based on the T or Z scores (e.g., less than −2.5 representing osteoporosis, between −2.5 and −1 representing osteopenia, and over −1 representing normal). In this manner, absolute bone mineral density values do not necessarily need to be calculated to diagnose the patient with osteoporosis.

As described herein, inventors discovered that imaging modality files acquired for reasons other than evaluation and/or diagnosis of osteoporosis related pathology provide a basis for automatic machine based learning, to correlate a grade calculated from the imaging modality files with a DEXA score. Optionally the grade is computed from a calculation of sub-grades performed for each one or a set of pixels having a common medial-lateral axial coordinate and/or a common cranial-caudal axial coordinate along a dorsal-ventral axis of a volume representation of the imaging data. For each patient, machine learning is based on grades calculated from imaging modality files (as described herein) and associated DEXA score(s) calculated from DEXA scans acquired for the same patient within a period of time that may be short enough such that bone mineral density changes are not statistically significant, for example, about 6 months. The training images for creating the classifier(s) may be based on a corpus of imaging modality files (e.g., conforming to the Digital Imaging and Communications in Medicine (DICOM) standard). In this manner, use of a general corpus of imaging modality files and/or medical records (including DEXA scores and/or CT scans performed for non-osteoporotic indications) may provide a base of data for the machine learning, which may enable correlation of grades calculated from CT image data to DEXA scores with a clinically significant accuracy (i.e., to screen and/or diagnose patients for osteoporosis or osteopenia), for example, as compared to special medical image files acquired to diagnose osteoporosis, such as DEXA.

An aspect of some embodiments of the present invention relates to systems and/or methods for selection of a group from a database for healthcare delivery, such as selection of a group from a corpus of CT image files for further evaluation of osteoporosis. Optionally a grade is computed for each patient, from a calculation of sub-grades performed for each one or a set of pixels having a common medial-lateral axial coordinate and/or a common cranial-caudal axial coordinate along a dorsal-ventral axis of a volume representation of the CT imaging data for each file of the corpus. The grade is correlated to obtain the score. Optionally, the group is selected according to a requirement applied to the DEXA score estimated from the grade calculated for each CT image file. Optionally, the requirement is a threshold value and/or range of values of the DEXA score, for example, below −2.5, or below −1, or other values. Alternatively or additionally, the requirement is a designated category from one or more category bins related to the estimated DEXA score, for example, osteoporosis diagnosis, osteopenia diagnosis, or abnormal, or other categories may be used. The selected group may undergo additional investigations related to osteoporosis, for example, DEXA scanning, blood work, physical examination, and/or other tests. In this manner, patients identified as possibly having osteoporosis or osteopenia may be identified using already acquired and/or stored CT image data (e.g., for clinical indications other than osteoporosis related pathology) to identify which patients should undergo further testing, instead of, for example, having all patients undergo DEXA scans.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term CT is sometimes interchangeable with the broader term imaging modality, as the systems and/or methods described herein may not be necessarily limited to CT, as other imaging modalities may be used as a basis for the methods and/or systems described herein, such as magnetic resonance imaging (MRI), standard X-rays, or other imaging modalities. The methods and/or systems may be applied to other imaging modalities that satisfy the following constraint: bones may be segmented from the acquired images.

As used herein, the term vertebra is sometimes interchangeable with the broader term bone or bone portion, as the systems and/or methods described herein may be adapted to segment and/or process other bones which may be correlated with the score (e.g., DEXA), for example, femur (e.g., head thereof), and radius.

As used herein, the term statistical classifier is meant in a broad sense, to include different methods and/or elements for correlating between the calculated grade and score, for example, a look-up table, a regression function, and other methods described herein.

As used herein, the terms DEXA and DXA are interchangeable.

Figure 2:
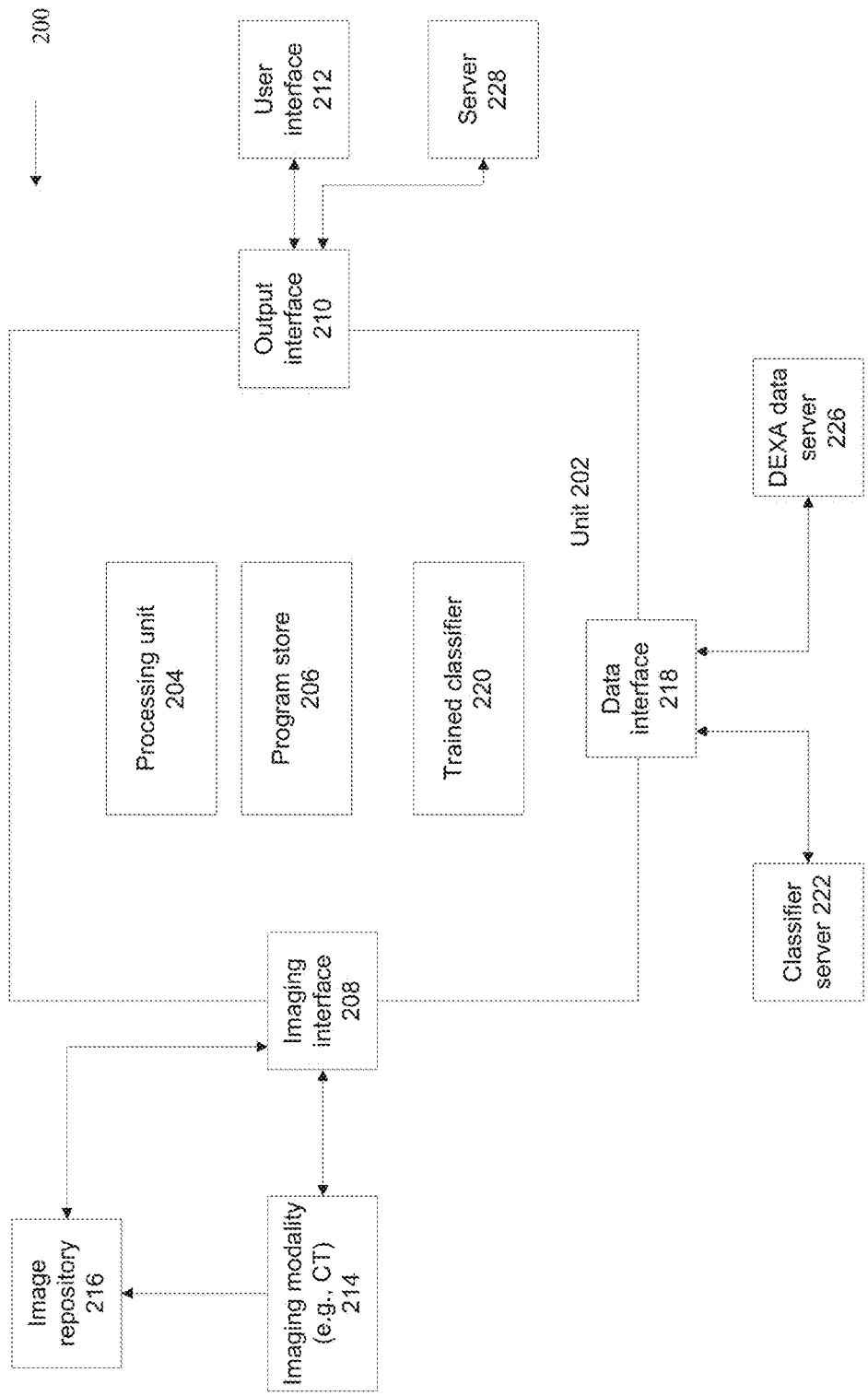
FIG. 2 is a block diagram of components of a system for estimating a DEXA CT imaging data, in accordance with some embodiments of the present invention.

Reference is now made to FIG. 1, which is a flowchart of a method for estimating a DEXA score (representing a relation to bone density values in a population) from CT imaging data, optionally a T-score and/or Z-score, in accordance with some embodiments of the present invention. Reference is also made to FIG. 2, which is a block diagram of components of a system that allows for CT imaging data to be analyzed and correlated to obtain the DEXA score, in accordance with some embodiments of the present invention. The system of FIG. 2 may execute the method of FIG. 1.

The systems and/or methods described herein may improve identification of bone portions (e.g., segmentation), such as vertebral bones, for example, as compared to existing methods that apply a simple threshold value, for example, pixel values above 200 HU to obtain a binary map of bones. The systems and/or methods described herein may segment the bone portion by excluding contrast material that would otherwise appear as bone.

The systems and/or methods described herein may improve DEXA score estimation (or other scores) in patients (e.g., having thin bones (e.g., due to osteoporosis)) for which the pixel associated values would otherwise be mistaken as not bones (e.g., values lower than the pixel value thresholds representing common bone values (e.g., 200 HU)). The systems and/or methods, by calculating multiple sub-grades over a volume and correlating the grade (calculated from the sub-grades), may improve accuracy of estimating the score, for example, in such cases, existing methods (e.g., based on the threshold) may incorrectly label such bones as not being bone.

The systems and/or methods described herein may improve performance of an existing system, for example, a picture archiving and communication system (PACS), and a radiology workstation. Improved performance may be, for example, in terms of reduced storage space, as existing stored images (e.g., CT) which may originally have been acquired for non-osteoporotic indications (or for osteoporosis related reasons) may be analyzed to estimate a DEXA score and/or to obtain a diagnosis (as described herein), which may reduce the need to store additional DEXA image data.

Optionally, imaging data acquired from patients undergoing routine imaging (e.g., CT scans) (e.g., not selected for diagnosis of osteoporosis) may undergo additional automatic screening analysis, such as in a by-the-way analysis routinely performed on every (or selected) acquired medical imaging data for every (or selected) patient, to estimate the score (e.g., T-score or Z-score related to DEXA imaging). The additional screening may be performed without requiring additional significant radiologist reading time. There may be some additional radiologist reading time, for example, to supervise the batch output and/or evaluate particular images. The patient may not require additional specialized imaging designed to screen and/or diagnose osteoporosis and/or osteopenia, which may expose the patient to additional radiation. The score estimation does not require dedicated scan settings, and/or additional hardware. The score estimation may be performed based on existing equipment, such as by installation of software modules to perform the methods described herein. The score estimation may be estimated before the patient experiences symptoms related to osteoporosis and/or fracture, instead of, for example, DEXA imaging.

System 200 includes a program store 206 storing code (to execute functions described herein), for example, a memory, and/or a storage device.

System 200 includes a processing unit 204 (e.g. one or more processors) to implement the code stored in program store 206.

System 200 optionally includes an imaging interface 208 for receiving imaging data of a computed tomography (CT) scan of a body of a patient containing at least a bone portion.

System 200 optionally includes an output interface 210 or communicating with a user interface 212, for example, a display, a touch screen, a keyboard, a mouse, and a voice activated unit.

One or more of processing unit 204, program store 206, imaging interface 208, and output interface 210 may be organized into a unit 202, for example, a standalone unit, software modules loaded onto an existing radiology workstation for processing medical image data after acquisition, a hardware module for plugging into the existing radiology workstation, a remote computer running software that receives the medical image data through a network connection, or other architectures.

At 102, imaging data of a computed tomography (CT) scan of a body of a patient containing at least a bone portion is received. Unit 202 may receive the imaging data from an imaging modality 214 (e.g., CT machine) and/or from an image repository 216 storing acquired CT images (e.g., a local storage and/or an external server, such as a PACS server), via imaging interface 208.

Optionally, the CT scan includes the bone portion(s) used for evaluation by DEXA based systems, for example, one or more of L1-L4 vertebra, femur bone, radius or other bones. The CT scan may include the abdomen and/or chest of the patient, or other body parts.

The acquired imaging modality files (used for training or being analyzed for risk) may be unsuitable for automatic diagnosis of osteoporosis by available computerized methods, such as not containing suitable data for calculation of BMD and/or other osteoporosis related measurements that may serve as a basis for diagnosis of osteoporosis. The CT data may not be necessarily collected as part of a CT scan ordered to measure BMD and/or diagnose osteoporosis, such as a quantitative CT scan, for example, calibration phantoms were not present during the CT scan. Optionally, the CT scan imaging data is inadequate for performing a quantitative computed tomography scan (QCT) for measurement of BMD.

Optionally, the CT scan is performed with settings selected for imaging of non-osteoporosis related pathology. Optionally, the CT scan has been ordered for diagnosis of non-osteoporosis medical conditions based on non-osteoporosis related signs and/or symptoms. The CT scan may have been ordered for a conventional clinical indication, for example, low dose CT scan of the chest to screen for lung cancer, CT scan to screen for colon cancer, standard non-contrast CT scan of the chest, intravenous (IV) contrast CT scan of the chest, standard non-contrast CT scan of the abdomen, IV contrast CT scan of the abdomen, oral contrast CT scan of the abdomen, pelvic CT scan, or other CT study protocols. The CT scan may have been ordered, for example, to help determine the cause of a bowel obstruction, to help diagnose appendicitis, assess complications of pancreatitis, screening for color cancer (i.e., virtual colonoscopy), evaluation of the urogenital system (i.e., CT urography), pre-operative work-up, or other reasons.

The imaging data of the imaging modality (e.g., CT) scan used by the methods and/or systems described herein may be inadequate and/or unsuitable for calculation and/or estimation of a bone mineral density (BMD) of the bone portion for diagnosis of osteoporosis.

At 104, the bone portion (e.g., one or more of L1, L2, L3, L4) are segmented from the imaging data, optionally by processing unit 204 implementing code stored in program store 206. Segmentation may be performed automatically by the code, without necessarily requiring manual user intervention. Alternatively or additionally, a region that includes the bone portion(s) is segmented and/or identified.

As used herein, the z-coordinate or z direction is defined as an axis in the head-feet direction, cranial-caudal axis, or up-down direction. The zero (0) z-coordinate is defined as the upper slice. The y-coordinate or y-direction is defined as an axis in the coronal direction, or front-back direction, or dorsal-ventral axis of the patient. The zero (0) y-coordinate is defined as the upper slice. The x-coordinate or x-direction is defined as an axis in the left-right direction, or medial-lateral axis, of the patient.

To segment one or more of the L1-L4 vertebrae, the imaging data is analyzed to identify a z-coordinate limitation of a region of interest (Z-ROI) that includes one or more of the L1-L4 lumbar vertebrae. For each z-coordinate slice, an x-coordinate limitation and/or y-coordinate limitation of the respective vertebrae (X-ROI, Y-ROI) are identified. The identified coordinates represent a region of interest (ROI) containing the segmented vertebrae. Optionally, surrounding organs and/or tissues having contrast agent (e.g., blood vessels, intestines) within the identified ROI are masked.

Inventors discovered that the accuracy of the estimated score obtained by correlation of the grade calculated based on the segmented vertebra, may be sufficiently accurate for clinical use, even when the segmentation accuracy is limited.

Figure 3A:
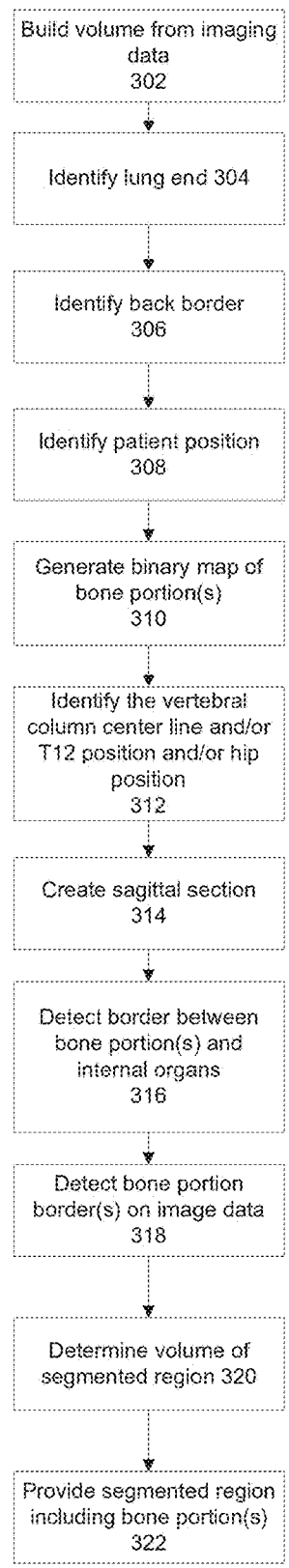
FIG. 3A is a flowchart of a method for segmenting a bone portion from imaging data for calculation of a grade to correlate with the DEXA score (for use with FIG. 1 and/or FIG. 2), in accordance with some embodiments of the present invention.

Different implementation for segmentation may be used. Reference is now made to FIG. 3A, which is a flowchart of an exemplary method for segmenting a bone portion, optionally one or more of L1-L4 vertebra, from imaging data (optionally CT scans) for calculation of a grade to correlate with the score (for use with FIG. 1 and/or FIG. 2), in accordance with some embodiments of the present invention. The method is designed to process images regardless of the use of contrast, and/or for different patient scan positions. The method is designed to create a segmented bone portion excluding contrast agent having pixel associated values representing bone (i.e., pixel values similar to bone value). The method may be executed by processing unit 204 implementing code stored within program store 206. When the imaging data does not include contrast (e.g., no contrast has been used during image acquisition), the method described with reference to FIG. 3B (below) may be used.

The segmentation method of FIGS. 3A and/or 3B may generate, alternatively or additionally to the segmented bone portion, an approximation ROI including L1-L4. The approximation ROI does not necessarily include a segmentation of each vertebra (e.g., may include an un-segmented portion including the bone portion). The approximation ROI may include part of the bone portion and other connected bones, for example, a region above the ROI (e.g., T12, or T11), and/or below the ROI (e.g., L5). The approximation ROI may be used for calculation of the grade.

The segmentation method may be designed to be robust in terms of identifying and/or adjusting to different scan orientations, by correctly localizing the segmented vertebra. It is noted that meta-data associated with the imaging data (e.g., tags as defined by the DICOM standard) may provide inaccurate information regarding the part of the body in the scan, or such information may not be available.

The segmentation method may be designed to be robust in terms of processing images containing or not containing contrast enhanced tissues and/or organs, for example, by excluding the contrast regions and/or avoiding incorrectly segmenting such contrast enhanced regions as bones. It is noted that meta-data associated with the imaging data (e.g., tags as defined by the DICOM standard) may provide inaccurate information regarding contrast use, or such information may not be available.

The segmentation method may be designed to be robust in terms of processing images regardless of the position of the patient relative to the scan table (e.g., prone or supine or other intermediate positions). It is noted that the lying position of the patient may not be available from meta-data related to the imaging data.

Since the resolution of the CT scan may vary for different scans, parameters may be defined in millimeters (mm), inches, or other units, and converted into number of pixels. Conversion may be adjusted (e.g., normalized) according to patient size which may be retrieved from DICOM tags (e.g., weight and/or height), and/or measured by code using the imaging data (e.g., measuring distance between ribs or other imaging data parameters).

At 302, a volume may be created based on the imaging data. The volume may include voxels, which may not necessarily be square. The volume includes pixels (or voxels) having x, y, and z coordinates.

At 304, the z-coordinate representing the end of one or both lungs of the patient is identified within the imaging data and/or volume. In most anatomies, and/or healthy anatomies, the end of the lung is expected to be located near the T12 vertebra. The exact location may vary, for example, based on lung size variations experienced during the breathing cycle. The L1-L4 vertebrae (located below the T12 vertebra) may be segmented guided by the identified z-coordinate.

The end of the lung(s) may be identified by the following exemplary method: Count the number of pixels representing lung tissue for each axial slice of the volume generated from the imaging data. Lung tissues may be identified according to Hounsfield Units (HU) values, for example, greater than about −900 and less than about −350. The z-coordinates are designated according to the largest identified decrease in the number of lung pixels between sequential axial slices, representing a drop between the maximal lung pixels and the location where the lung ends.

Figure 5:
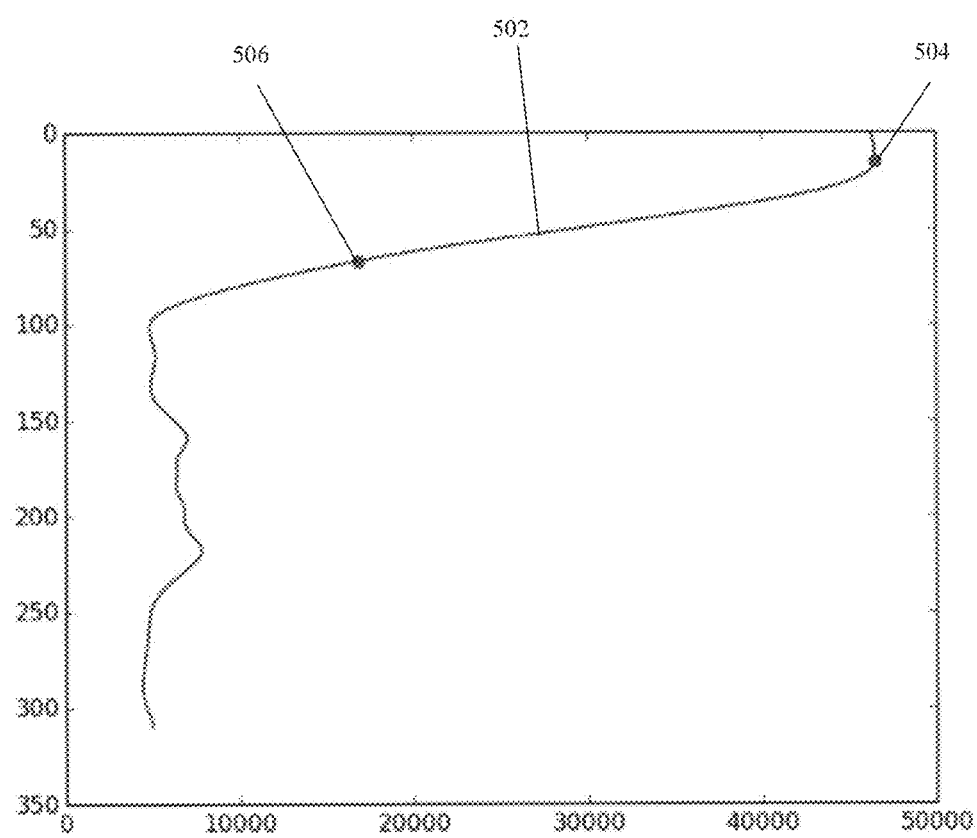
FIG. 5 is an example of a graph depicting the number of lung pixels (along an x-axis) per z-axis of a CT scan, useful for identifying the end of a lung of a patient, in accordance with some embodiments of the present invention.

Reference is now made to FIG. 5, which is an example of a graph having a line 502 depicting the number of lung pixels (along an x-axis) per z-axis of a CT scan, useful for identifying the end of a lung of a patient, in accordance with some embodiments of the present invention. The z-coordinate corresponding to 504 represents the identified maximal lung. The z-coordinate corresponding to 506 represents the identified lung end.

Reference is now made to FIG. 6, which includes two example CT scans (sagittal section shown) with marked locations where lungs end, in accordance with some embodiments of the present invention. Image 602 is a scan of a patient lying on his/her back. Line 612 represents the scanning table/bed. Image 604 is a scan of a patient lying on his/her stomach. Lines 606 and 608 mark the identified end of the lung (according to the methods described herein). Line 610 marks the z-coordinate of maximal lung pixels (according to the methods described herein). Regions 614 represent intestines filled with contrast, appearing as bone, which are excluded from the segmentation using the methods described herein.

Referring now back to FIG. 3A, optionally, at 306, a border representing the back of the patient is identified. The back may be identified on a sagittal section of the imaging data (and/or volume). The identified back border may be used as a guide to segmentation of the L1-L4 vertebra, as the vertebra are expected to be located in near proximity to the back border (within the body of the patient). The back border (e.g., represented as a line) may be identified based on the assumption that there are no organs or tissues located behind it (i.e. outside the body of the patient), and/or that the back border does not contain contrast.

An example method to identify the back line border from sagittal slice(s) includes: Defining a width along the x-axis direction around the mid-sagittal line, for example, about 75 mm to the left and right (for an average adult—other widths may be used for children or large or smaller adults). The width is selected to include the vertebral column within the width, and to exclude the ribs (e.g., the outer portions appearing on the respective slice). A binary map is created from the sagittal image data, based on pixels assigned a binary value (e.g., True, 1, or other values) when a number of pixels is above a predefined threshold, the pixel in the x-axis for each pixel in the y-z coordinates being above a value representing bone (e.g., about 200 HU). The predefined threshold of the number of pixels may correspond to about 3 mm. It is noted that contrast containing organs and/or tissues appearing as bones are excluded at a different stage. The large connected component is identified. The bed line (i.e., representing the scanning bed on which the patient is lying) which may appear as bone (e.g., based on similar HU values) is removed. The back border is identified based on the pixels furthest along the y-direction (i.e., towards the bed line) in the sagittal map. A smoothing filter may be applied to the identified back border to generate a line.

Optionally, at 308, the lying position of the patient relative to the scanning table (or bed) is detected. The lying position of the patient may be used to convert the imaging data to a common format for analysis, for example, from the supine to the prone position or from the prone to the supine position, or maintain the imaging data in the current format.

The exemplary method described with reference to block 306 may be repeated using a second (optionally larger) window size selected to include the ribs. A second back line is identified.

The proximity (e.g., in terms of pixel coordinates) of the first and second back lines are compared. The position of the patient relative to the scan table is identified according to the proximity comparison. When the patient is lying on his/her back on the table (supine), the proximity is close or the same (i.e., small or no changes between the first and second lines). When the proximity is relatively larger (i.e., second line moved further away from the table) the patient is identified as lying on his/her front (prone). In such a case, the second line is moved due to the appearance of the ribs in the image.

Alternatively or additionally, the z-coordinate representing the end of the lung is identified for both the first and second sets of processed image data. When the end of the lung is different between the first and second sets, the movement may represent that the patient is lying on his/her front, i.e., that the identified back line is actually the front of the patient.

Optionally, when the patient is identified as being in a position different than a predefined common position (e.g., patient in the prone position (or another position other than supine) which is different than the common supine position), the pixel data is adjusted. Optionally, the y-coordinates of the imaging data is inverted.

Figure 7:
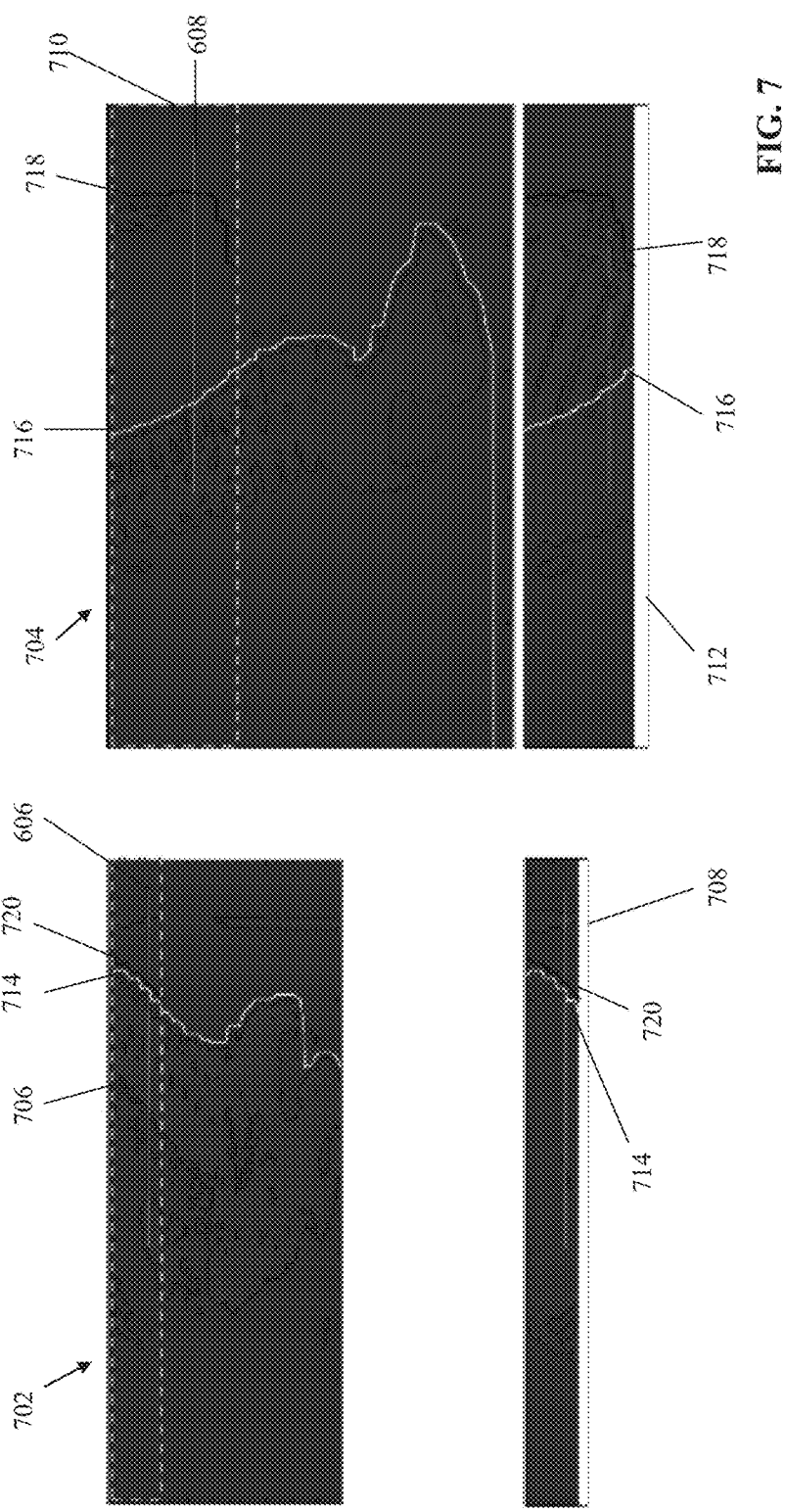
FIG. 7 includes two example binary maps of the CT scans of FIG. 6, in accordance with some embodiments of the present invention.

Reference is now made to FIG. 7, which includes two example binary maps of the CT scans of FIG. 6 generated based on the method described with reference to blocks 306-308, in accordance with some embodiments of the present invention. Binary map 702 is derived from image 602, and binary map 704 is derived from image 704. Binary maps 702 704 have been generated using a width of 75 mm to each direction (to exclude the ribs) from the mid sagittal line. Lines 606 and 608 mark the identified end of the lung (derived from the corresponding CT image). Binary maps 708 and 712 are generated with a larger width selected to include the ribs. Maps 708 and 712 are respectively generated from section 706 of map 702 and section 710 of map 704. First and second back lines are identified in each binary map (using the methods described herein). A first back line 714 has been identified in binary map 702 (also shown in map 708), and a second back line 720 has been identified in binary map 708 (also shown in map 702). A first back line 716 has been identified in binary map 704 (also shown in map 712), and a second back line 718 has been identified in binary map 712 (also shown in map 704).

As seen on map 702 and map 708, lines 714 and 720 are close to one another, representing that the patient is lying on his/her back. As seen on map 704 and map 712, lines 716 and 718 are relatively far from one another, representing that the patient is lying on his/her stomach. Pixels and/or image data related to map 704 may be inverted relative to the y-axis to covert the image data to the common format, similar to the patient lying on his/her back.

Referring now back to FIG. 3A, at 310, a binary map of the vertebral column is generated. The binary map may include a portion of the ribs attached to the vertebrae. The creation of the binary map may be guided by the identified back line, to help exclude contrast containing tissues and/or organs from the segmentation.

Optionally, the binary map is generated in a coronal view.

Optionally, the coronal binary map is generated within a region the identified border large enough to include the vertebra and optionally connected rib portions, while excluding other nearby tissues, for example, up to about 50 mm from the identified back line (for an average adult).

The binary map may be generated by assigning a binary value (e.g., true, 1) to pixels in the region having a value above a threshold representing bone, for example, about 200 HU. Pixels having a value below the threshold may be assigned a different value (e.g., false, 0).

Figure 8:
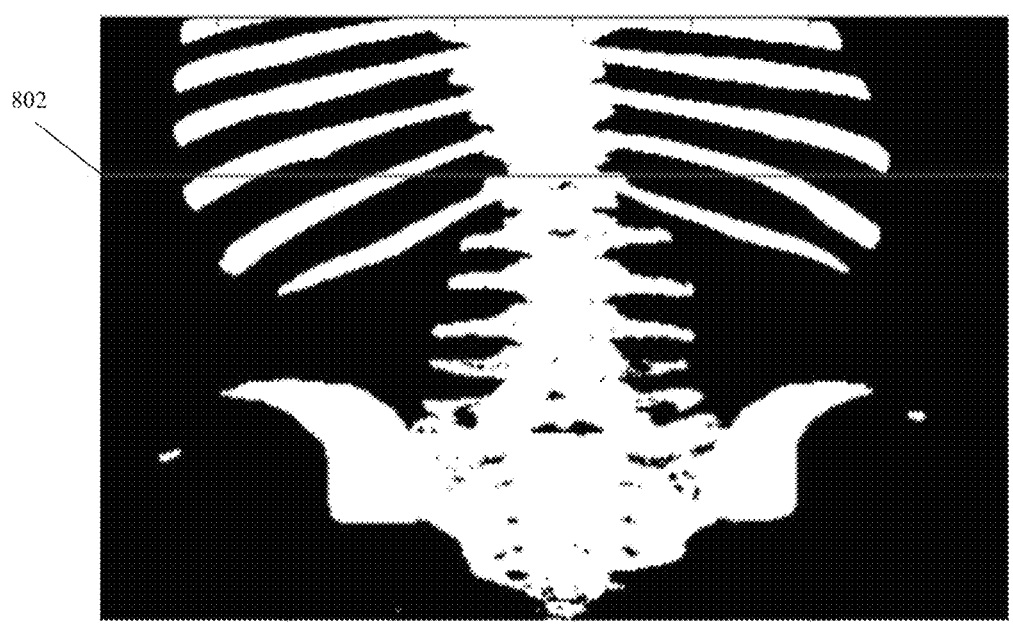
FIG. 8 is an example of a coronal binary map, in accordance with some embodiments of the present invention.

Reference is now made to FIG. 8, which is an example of a coronal binary map, in accordance with some embodiments of the present invention. Line 802 represents the end of the lung (as described herein).

Referring now back to FIG. 3A, at 312, a component including the vertebral column is identified, optionally from the coronal binary map. The vertebral column may be identified as the largest connected component that crosses the z-coordinate defining the end of the lung.

The vertebral column may be identified by the following exemplary method: Define a box filter having a size related to the data resolution, for example, 20 mm in the z-direction and 10 mm in the x-direction. The filter is applied to the coronal binary map (or the CT image data) to obtain a gray image. A binary image is created from the gray image, by applying a threshold related to the box filter size, for example, 90%. The threshold is selected to select relatively large objects, for example, to achieve a dilation-like effect. A connected component labeling process is applied to the binary image, to select the largest component that crosses the z-coordinate representing the end of the lung. The box filter is re-applied, using a threshold selected to create an erosion-like effect, for example, 10%. The largest connected component is a binary map having values representing bone or other.

A central line of the largest connected component is identified. The central line guides creation of a sagittal section. Side boundaries of the largest connected component are identified. The side boundaries are used for segmentation of the vertebra. Optionally, the lines of the largest connected component are smoothed, for example, by applying a median filter.

Optionally, the z-coordinate of the hip and/or L5 is identified on the coronal binary map, optionally relative to the femur neck. Optionally, the z-coordinate of the T12 vertebra is identified on the coronal binary map. The locations may be detected by comparing the full coronal binary map (or another image derived from the CT image data) to the identified largest component, and identifying on the largest component the location corresponding to the location on the coronary binary map of the connection of the lowest rib (representing T12) and/or where the coronal binary map width is the largest (representing the hip or L5). The L1-L4 vertebra are located between the identified locations, within the largest connected component (i.e., below T12 and above the hip or L5). Segmentation is performed according to the identified region including L1-L4.

Figure 9:
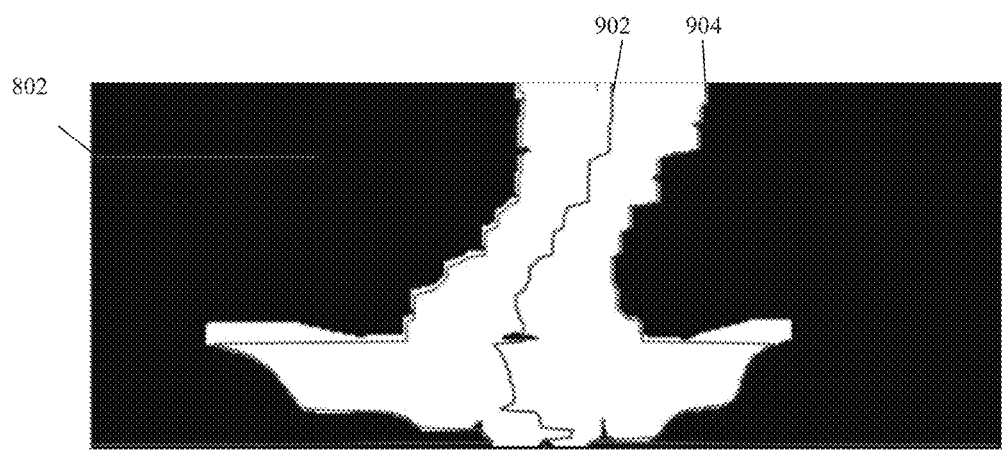
FIG. 9 is a processed image of the coronal binary map of FIG. 8, in accordance with some embodiments of the present invention.

Reference is now made to FIG. 9, which is a processed image of the coronal binary map of FIG. 8, including the identified largest connected component, in accordance with some embodiments of the present invention. Line 802 represents the end of the lung. Line 902 represents the mid line. Lines 904 represent the sides of the largest connected component.

Figure 10:
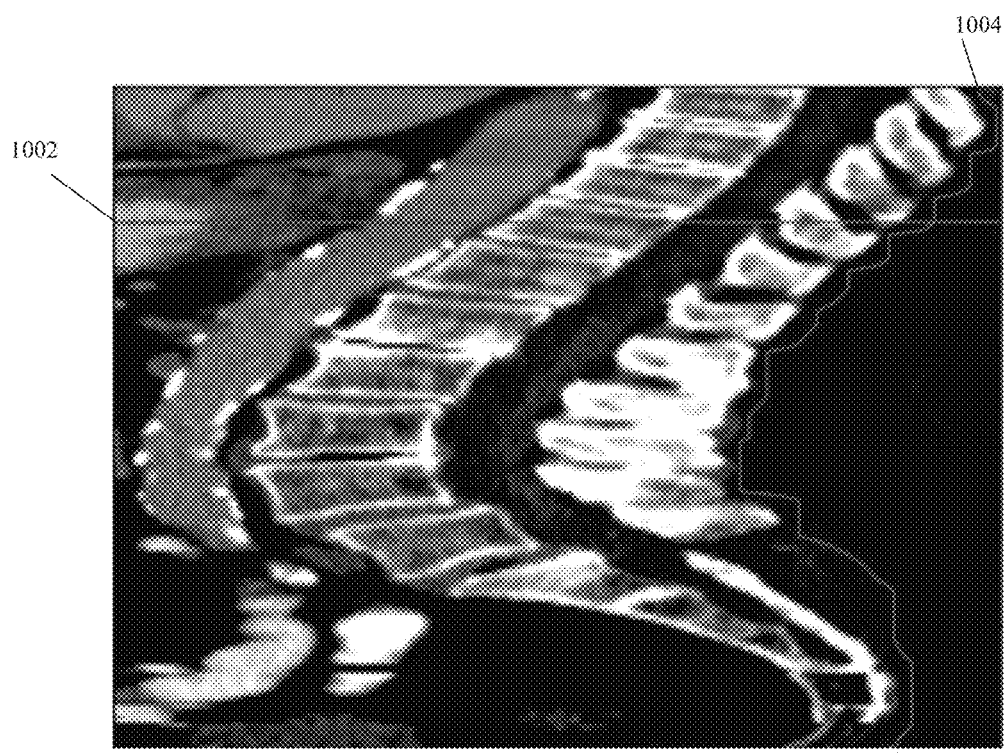
FIG. 10 is an example sagittal section of a CT image including a marked back of the patient, in accordance with some embodiments of the present invention.

At 314, a sagittal section of the imaging data is created. The sagittal section is created to slice through the vertebral column. FIG. 10 is an example sagittal section of a CT image including a marked back line of the patient 1004, and a marked line 1002 representing the end of the lung. The vertebrae for segmentation are located within the region defined by lines 1002 and 1004.

When the patient is not lying straight, the vertebral column is transformed to be straight, as described herein.

Optionally, noise is removed from the imaging data. The noise may be removed for each z-coordinate alone the x,z line, by selecting y,z lines. Averaging may be performed to reduce noise, for example, by 1 mm in each direction. Other methods of denoising may be applied, for example, a median filter.

At 316, a border between the vertebral column of the patient (e.g., the vertebra body portion of each vertebra) and other organs in near proximity is identified within the sagittal section. The border may be at the anterior edge of the vertebrae. Another border at the posterior edge of the vertebrae may be identified. The second border may be between a vertebral foramen (and/or the spinal cord) and the vertebral column (or the vertebral bodies). The identified vertebral column may include vertebral bodies and excludes vertebral pedicles and processes. Alternatively, the second border is identified at the posterior edge of the vertebra (e.g., which may be in proximity or the same as the back border). The second border may include the vertebral pedicles and processes of the vertebrae.

The borders between the vertebral bodies and other tissues and/or the vertebral foramen may be identified as a y,z line. The line defines a region for segmentation that excludes contrast effects. Since the use or lack of use of contrast may be unknown, an exemplary method is designed to operate regardless of whether contrast exists or not: The border between the spinal cord and the vertebral section is detected, optionally using a binary map that represents bones (e.g., values above 81 HU to include trabecular bone portions) and a binary map of spine-like values (e.g., between −65 and 65 HU). The identified patient back line may be used as an initial location for searching, as the back line represents the spinous process portion of the vertebrae. Moving in a direction from the back line towards the front of the patient's body, the vertebral foramen (which houses the spinal cord) is located near the back line. The border between the vertebral foramen and the vertebral body may identified by searching for a gradient line, which is expected to be approximately parallel to the border. For example, a binary map may be created using different threshold values, for example, 100 HU, 150 HU, and other values, optionally with applied dilation filters. The border may be identified according to a location where the width of the vertebral column is the smallest and close to a constant value (along a cranial-caudal direction) having a low standard deviation.

Figure 11:
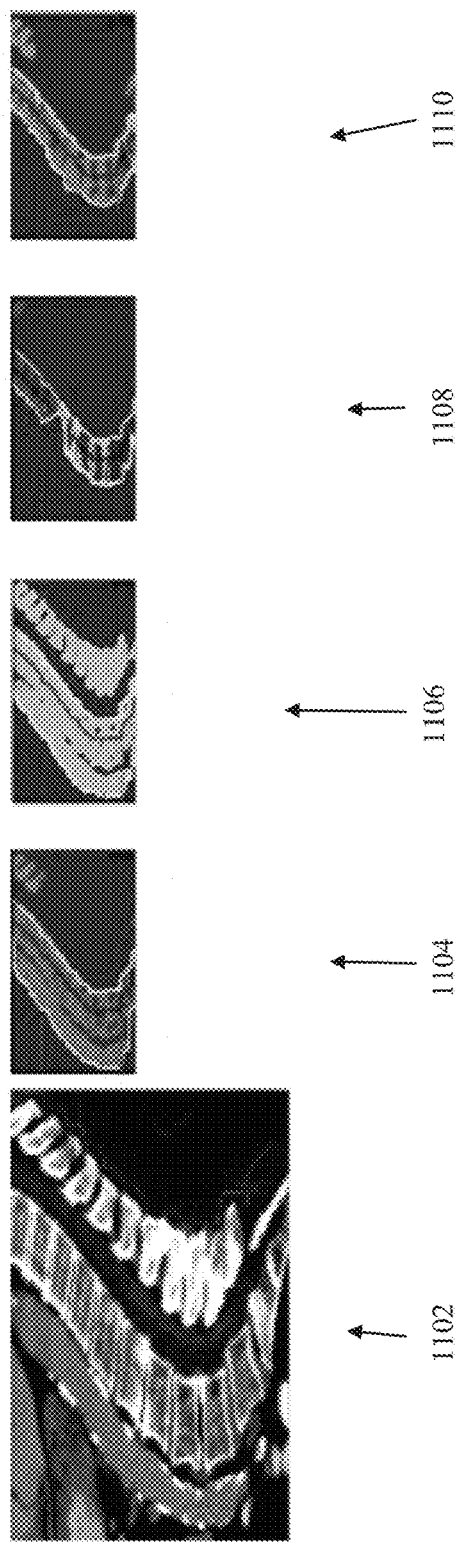
FIG. 11 includes examples of images that graphically depict methods to detect the edge between the vertebral body and the internal organs, in accordance with some embodiments of the present invention.

FIG. 11 includes examples of images that graphically depict methods to detect the border between the vertebral bodies and the internal organs, in accordance with some embodiments of the present invention. Image 1102 is a CT sagittal image (e.g., as shown in FIG. 10). Binary maps 1104, 1106, 1108, and 1110 are generated using different thresholds. Map 1104 is created using a binary threshold of 100 HU. Map 1106 is created using a binary threshold of 100 HU and 1 dilation iteration. Map 1108 is created using a binary threshold of 150 HU. Map 1110 is created using a binary threshold of 150 HU and 1 dilation iteration.

Referring now back to FIG. 3A, at 318, the borders of one or more of the L1-L4 vertebral (or vertebral body portions) are identified, optionally on the imaging data. Identification of the borders of the L1-L4 may be guided by the identified T12 and Hip (or L5) z-coordinates (i.e., as L1-L4 lie below T12 and above L5). It is noted that even an inaccurate estimation of the position of the L1-L4 may provide accurate scoring results. The identification of L1-L4 may be performed on a coronal and/or sagittal section of the imaging data.

Optionally, the identified border of vertebral bodies (e.g., block 316) is used to guide a transformation of the vertebral bodies of the imaging data to a vertical alignment. The vertical alignment may be transformed according to calculated gradients between each vertebral body and the spinal column. On the vertical alignment, borders of at least one of the L1, L2, L3, and L4 vertebral bodies may be identified. Based on the identified borders of the vertical alignment, the vertebral bodies on the imaging data may be marked and/or identified on a mapping from the vertical alignment back to the imaging data.

Figure 12:
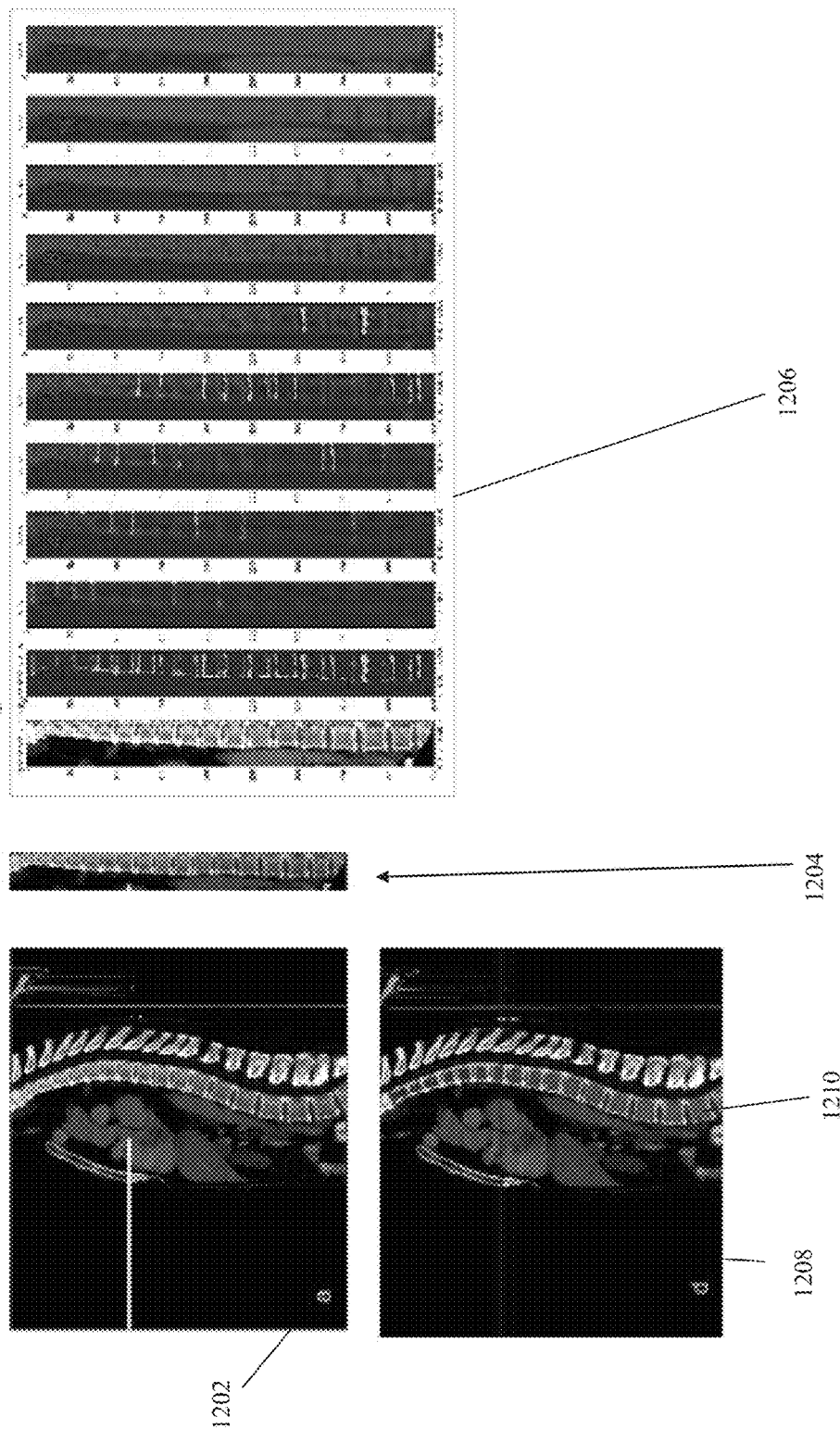
FIG. 12 includes another example of images that graphically depict methods to detect the edge between the vertebral body and the internal organs, in accordance with some embodiments of the present invention.

FIG. 12 includes another example of images that graphically depict methods to detect the edge between the vertebral body and the internal organs based on transformation of the vertebral bodies to a vertical alignment, in accordance with some embodiments of the present invention. Image 1202 is the starting sagittal CT image. Vertebral body portions are transformed into a vertical alignment as shown in image 1204. Different thresholds are applied to create multiple binary images 1206 of the vertical column, for example, from 321 HU to 81 HU. New vertical lines are searched for and identified in successive binary images, based on location within a reasonable distance from each other, for example, between about 20 mm and 100 mm. The vertical lines represent disks between vertebral bodies. A transformation (and/or mapping) is applied from the vertical column back to the sagittal section 1208 for marking the vertebral bodies 1210.

Alternatively or additionally, the discs between the vertebral bodies may be identified and serve as a guide for the border.

Figure 13:
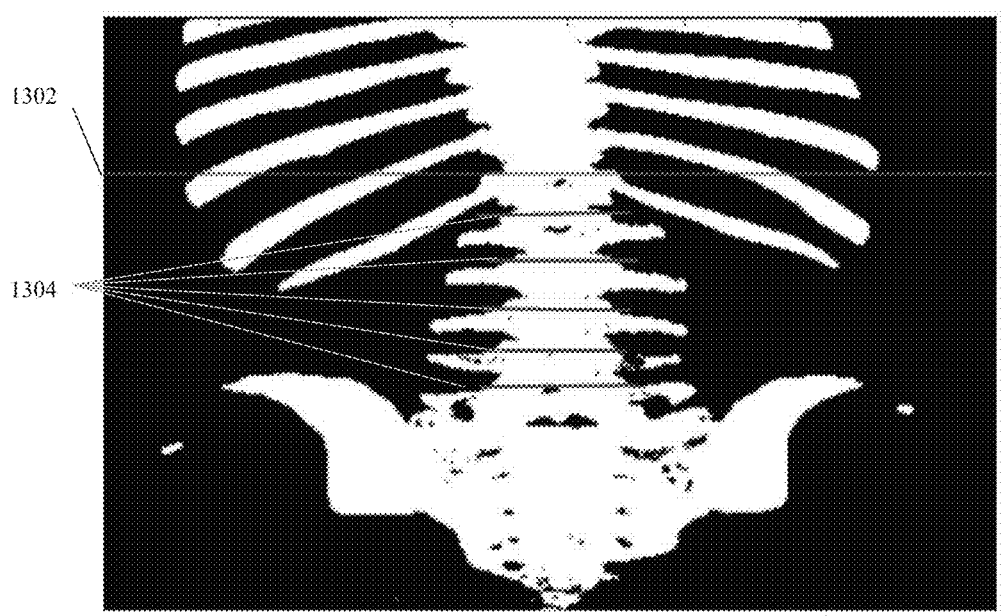
FIG. 13 is a binary map representing another example of a method to mark the border between vertebrae, in accordance with some embodiments of the present invention.

Alternatively or additionally, bumps on the generated coronal binary map may be identified and serve as a guide for the border. FIG. 13 is a coronal binary map representing another example of a method to mark the border between vertebrae, in accordance with some embodiments of the present invention. Borders 1304 may be identified as the region between the bumps (representing rib portions connecting to the vertebra), located below the end of the lung line 1302.

Alternatively, the borders between vertebral bodies are estimated by dividing the z-coordinate values between the identified T12 location and the identified hip or L5 location. Such an estimate may be used where the borders are difficult to accurately define, for example, in low resolution CT scans, or patients having curved spines (e.g., scoliosis).

Figure 14:
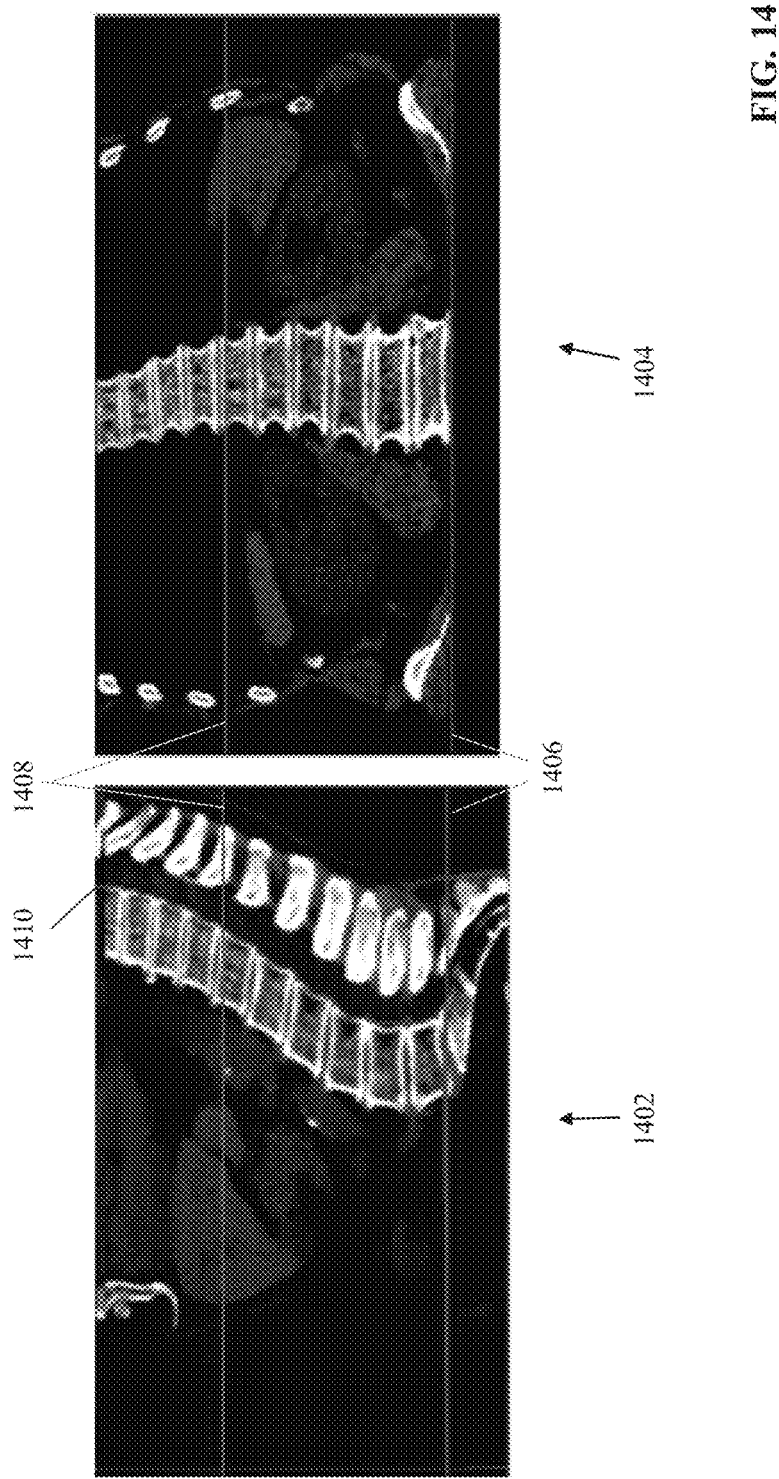
FIG. 14 is an example of a sagittal and a coronal section of a CT scan of a patient with markings for segmentation of the vertebra, in accordance with some embodiments of the present invention.

Reference is now made to FIG. 14, which is an example of a sagittal 1402 and a coronal section 1404 of a CT scan of a patient with markings for segmentation of the vertebra, in accordance with some embodiments of the present invention. Lines 1408 define the end of the lung. Line 1410 defines the border between the vertebral bodies and vertebral foramen (or spine). Lines 1406 are located below L5 and/or the hip. Coronal section 1404 was created by extracting y,z lines along a path which is 15 mm to the left of line 1410 of sagittal image 1402. L1-L4 may be segmented, as being in the region defined by lines 1408, 1410, and 1406.

Referring now back to FIG. 3A, at 320, the volume for calculation of the grade is identified. The volume is identified according to the x, y, and z coordinates. In the z-coordinate, as being between the identified location of T12 and the hip (or L5). In the x-coordinate, as being along the sides of the identified largest connected component in the coronal view (e.g., x varied along z). In the y-coordinate, as being between the border of the vertebrae and the internal organ edge and the maximal y value defined by the border of the back of the patient (e.g., y varied along z). The volume may be the approximation ROI, as described herein.

At 322, the volume (which includes the bone portion) and/or the segmented bone portions (e.g., the vertebrae) and/or the approximation ROI is provided for computation of the grade.

Figure 3B:
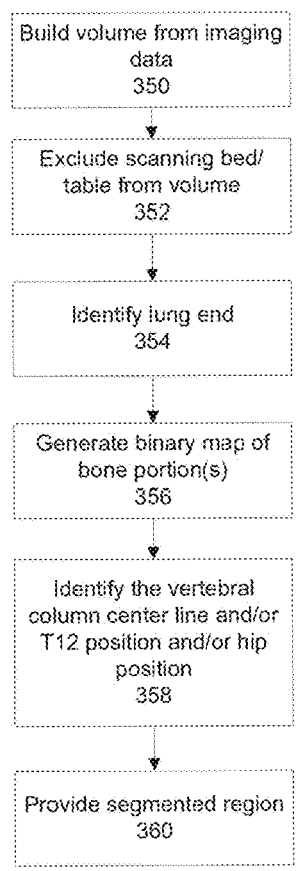
FIG. 3B is a flowchart of a method for segmenting the bone portion from imaging data when the imaging data does not include contrast agent affecting the calculation of the grade to correlate with the DEXA score (for use with FIG. 1 and/or FIG. 2), in accordance with some embodiments of the present invention.

Reference is now made to FIG. 3B, which is a flowchart of a method for segmenting the bone portion from imaging data when the imaging data does not include contrast agent affecting the calculation of the grade to correlate with the DEXA score (for use with FIG. 1 and/or FIG. 2), in accordance with some embodiments of the present invention. The lack of contrast agent (or contrast agent used in body parts that are excluded from the segmented volume, such as between the lumbar vertebra and the nearby skin), or insufficient amount of contrast agent to affect the grade calculation, may be identified, for example, from a field related to the imaging data (e.g., DICOM tag), manually entered by the user, and/or automatically detected by software. The method of FIG. 3B may be implemented by the processing unit executing code stored in the program store, as described with reference to FIG. 3A.

The method generates a segmented volume and/or region for computation of the grade along the y-axis, as described herein. The method does not necessarily segment along the y-axis, as the soft tissues (i.e., non-bone) are excluded from calculations by other methods, for example, by the threshold of pixel associated values as described herein. The use of the threshold may replace image subtraction methods to exclude contrast related regions (which may appear as bone), as such contrast related regions are not present. The method excludes the scanning table (or bed).

At 350, a volume is created from the imaging data, for example, as described with reference to block 302 of FIG. 3A.

At 352, the scanning bed (or table) may be excluded from the created volume. The scanning bed may include pixel associated values (e.g., HU values) which may be in the grade calculation range. As such, the scanning bed is excluded to prevent inclusion in the grade calculation.

Exclusion of the bed may be performed by a heuristic based method. Values may differ, for example, according to the scanning modality and/or scanner type (e.g., model) used.

An exemplary procedure (other procedure may be used) for exclusion of the bed includes: for the volume (or sagittal slices) a binary map is built using a threshold of about >−600 HU of pixel associated values. The binary map includes the body of the patient as a single large connected component. The bed is a separate component. The largest component is selected from the binary map, and/or the upper component (along the y-direction) is selected, to include the body of the patient while excluding the bed. The binary map may be applied to the volume to generate another volume that excludes the bed.

The volume with the excluded bed may be used for the other blocks, and/or the bed may be excluded in other blocks using the binary map.

At 354, a lung(s) end is identified, for example, as described with reference to block 304 of FIG. 3A.

At 356, a binary map of the bone portion is generated, for example, as described with reference to block 310 of FIG. 3A.

At 358, a largest connected component (which may be included as an approximation ROI) is selected, for example, as described with reference to block 312 of FIG. 3A. Alternatively or additionally, the vertebral column is identified according to an identification of the vertebral column center line and/or the T12 position and/or the hip position, as described herein, for example, with reference to block 312.

At 360, the segmented region and/or approximation ROI is provided for calculation of the grade. The segmented ROI may be limited in the Z direction by T12 and by the hip. X-direction limitations may be defined according to the binary map (e.g., of block 356). Y-direction limitations may be defined according to the binary map of block 352. It is noted that soft tissues of the patient may be excluded by thresholding in the y-direction.

It is noted that when the segmentation method (e.g., of FIGS. 3A and/or 3B) is detected to have failed, a different segmentation method may be used, or the user is provided with an indication that the segmentation failed (e.g., a message is presented on the display). Failure may be due to, for example, incomplete ability of the code to process the imaging data such as due to patient anatomical abnormalities (e.g., patient vertebrae are too big or too small for correct processing). Failure may be due to, for example, image scan acquisition performed in range or parameters that lead to segmentation processing failures, for example, image resolution too low to segment.

Referring now back to FIG. 1, at 106, one or more grades are computed based on pixel associated values from the segmented bone portion and/or the identified volume (e.g., block 320 or block 360).

Figure 22:
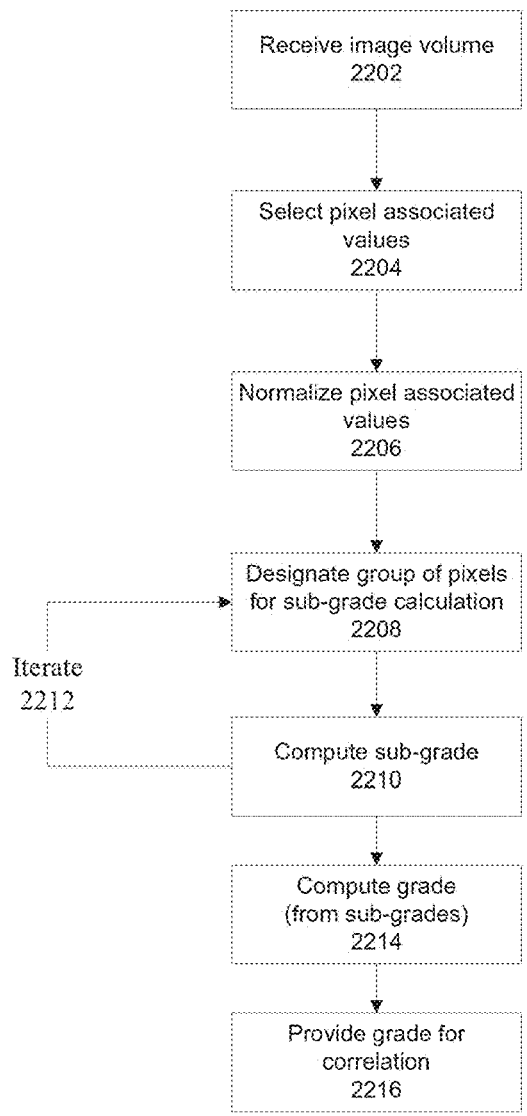
FIG. 22 is a flowchart of an exemplary algorithm for calculating the grade, in accordance with some embodiments of the present invention.

Reference is now made to FIG. 22, which is a flowchart of an exemplary algorithm for calculation of the grade, in accordance with some embodiments of the present invention. The algorithm may be stored as program instruction code in program store 206, implementable by processing unit 204.

At 2202, a volume of imaging data for grade calculation is received, optionally the volume which includes the bone portion(s) and/or the segmented bone portions of block 104.

Figure 15:
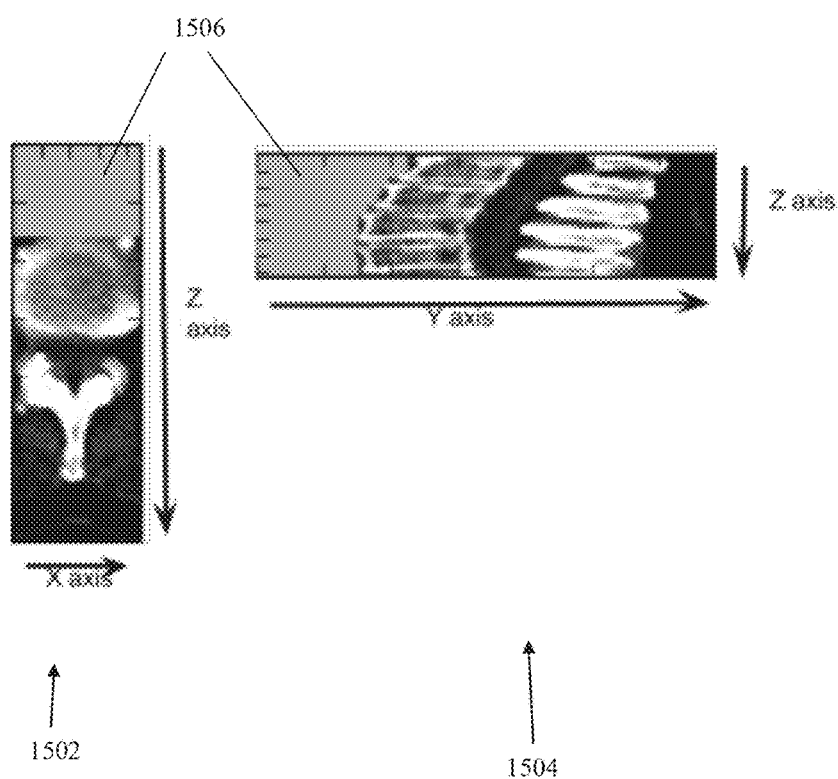
FIG. 15 is an example of a sagittal and a coronal section of a CT scan of a patient depicting regions to exclude from the calculation of the grade, in accordance with some embodiments of the present invention.

FIG. 15 is an example of an axial 1502 and a sagittal 1504 section of a CT scan of a patient depicting regions 1506 (filled in with grey) to exclude from the volume used for calculation of the grade, in accordance with some embodiments of the present invention. The regions for exclusion were identified by the method described with reference to FIGS. 3A-3B.

The volume for calculation of the grade includes the desired one or more bone portions, optionally one or more of the L1, L2, L3, and L4 vertebra, optionally the vertebral bodies thereof. It is noted that other volumes including other bones may be used instead or in addition.

Referring now back to FIG. 22, at 2204, pixel associated value(s) for computation of the grade are selected, for example, based on pre-defined system configurations, based on an automatically analysis of the imaging data, and/or based on manual use selection. The pixel associated values may be image intensity values, HU values, or other values derived from the pixel data. Combinations of values may be used. Factors for selection of the pixel associated values include, for example, image quality, image resolution, image color, and imaging modality. Factors for selection of the pixel associated values may be based on obtaining the most accurate correlation with the score.

Optionally, at 2206, the pixel associated values of the imaging data are normalized, for example, to a scale of 0-1, or other values. The normalization may be performed on a linear scale, according to a Gaussian distribution, or other normalization factors.

At 2208, a group of pixels for calculation of a sub-grade for computation of the grade is designated. Groups may be selected iteratively for sequential sub-grade computations, from which the final grade is computed. Alternatively or additionally, sub-grade computations may be performed in parallel (e.g., by the processing unit parallel processing the imaging data). Alternatively or additionally, the grade is directly computed without the intermediate sub-grade computation step (e.g., by the processing unit processing the imaging data).

Pixels located along a y-axis representation of the imaging data (e.g., of the created volume), which may be defined as the front-back (ventral-dorsal) direction of the patient may be designated. One or a set of pixels having a common x and/or z co-ordinate, along the y-axis may be designated.

Pixel groups may be selected according to segmented vertebra, according to the imaging data considered as a whole volume, according to all vertebra, according to a division of the vertebral column where each division includes one or more partial vertebrae, or other methods.

At 2210, the sub-grade is computed for each group of designated pixels. Optionally, a sub-grade is computed for each group, by a summation of the pixel associated values along the y-axis, optionally for each x and/or z coordinate or set of coordinates, as designated. Optionally, the sub-grade is computed as an average of the pixel associated values per designated group. The sub-grade may be computed for pixels having a value above a predefined threshold. The predefined threshold may represent bone, for example, in the range of about 150-300 HU, for example, about 200 HU.

Optionally, at 2212, blocks 2208 and 2210 are iterated, to compute sub-grades for different designated pixel groups. Alternatively, the grade is directly computed without the intermediate sub-grade computation.

The sub-grades may be computed for one set of x,z coordinates, or for multiple (or all) sets of x,z coordinates of each vertebra, generating multiple sub-grades for each vertebra. The sub-grades may be summed or averaged to result in a final grade for the vertebra, as in block 2214.

Alternatively or additionally, the sub-grade is computed for the relevant pixel associated values, along the entire volume of each vertebra, or along the entire volume of all vertebrae.

At 2214, the grade is computed from the multiple sub-grades. One or more methods may be used to compute the grade.

The grade computation is selected to provide a more accurate correlation (i.e., that other computation methods along different axes) with the score calculated by DEXA based methods that generate a 2D AP or PA (anterior-posterior or posterior-anterior) projection image of the patient (i.e., the patient may be prone or supine relative to the scan table), in which the energy of the DEXA scanner travels along the ventral-dorsal axis of the patient.

The grade may be computed in one or multiple ways (e.g., combination of multiple methods). The method for computation may be selected according to the received imaging data. For example, depending on the quality of the imaging data, the resolution of the imaging data, and which anatomical bone portions are clearly visualized.

Exemplary methods for computing the grade from the sub-grades (or directly) include:

- Selecting the minimal sub-grade computed for each vertebra. Such calculation may produce 4 sub-grades for the 4 vertebra. Each sub-grade may be correlated to obtain multiple sub-scores. The lowest correlated sub-score may be designated as a final result.
- Average the sub-grades computed for multiple vertebrae. Such calculation may produce a single final grade by averaging the multiple sub-grades calculated for the 4 vertebra. Each vertebra may have one or more computed sub-grades.
- Computation based on multiple defined sub-sections each including portions of multiple vertebrae. Subsections may be defined along the z-axis, for example, an upper half, a lower half, and a middle half (e.g., ¼ and ¾ of the length of the volume along the z-axis). Each sub-section may include portions of one or more vertebra, instead of an entire vertebra. A sub-grade calculation may be performed for each sub-section, generating multiple sub-grades, the lowest of which may be selected, and/or the average of the multiple sub-grades may be calculated to generate a single final grade representing all sub-sections.
- Sub-grade computation for a single predefined vertebra. For example, the sub-grade may be calculated for the L1 vertebra, and not for other vertebra. The sub-grade may be the final grade, or used in combination with other methods.

Multiple methods may be combined. For example, when multiple sub-grades are computed by different methods, the average final grade may be computed from the sub-grades and/or the minimal value final grade may be selected from the sub-grade, to provide the single final grade for correlation.

At 2216, the final grade is provided for correlation.

It is noted that the grade computation methods described herein may achieve accurate correlated scores, even when the segmentation is not accurate, and/or even when borders between vertebra are incorrect, and/or even when mis-registration of the vertebra occurs (i.e., detection of different vertebra).

It is noted that the systems and/or methods described herein, by using 3D imaging data, may segment and calculate grades for bones that would otherwise not be sufficiently visible for processing by 2D imaging methods such as DEXA. For example, the cervical and/or thoracic vertebra, may not be fully visible, obstructed by ribs and/or the sternum. Use of such bones may further improve the accuracy of the generated score, for example, by selecting the grade of a thoracic vertebra when such grade is lower than the calculated score of the lumbar vertebrae.

Reference is now made to FIGS. 16A-16F, which include images depicting calculation of the grade, in accordance with some embodiments of the present invention. Image 1602 is a sagittal section of a volume generated from CT imaging data. Image 1604 is based on image 1604, with a region 1616 excluding organs located frontal to the vertebrae (shown as grey). Image 1606 is an axial section of the imaging data, including region 1616. Image 1608 is based on image 1602, including only pixels having values above 200 HU. Image 1610 is generated based on a summation of the pixel associated values in the volume along the y-axis, optionally for each x,z-coordinate. Image 1612 depicts image 1610 divided into regions including the 4 vertebra (L1-L4). The grade may be calculated using image 1612, for example, by averaging each of the regions, averaging the entire volume, or averaging portions that include parts from multiple regions (e.g., half of the first region and half of the second region).

Referring now back to FIG. 1, at 108, the calculated grade(s) is correlated with a score(s) representing a relation to bone density values acquired based on DEXA methods. The score may represent a relation to a healthy young population (e.g., T-score) and/or to a demographically similar population (e.g., Z-score). Alternatively or additionally, the calculated grade(s) is correlated to bone mineral density (BMD) values, optionally BMD calculated based on DEXA methods.

Optionally, the correlation as described herein is performed using specialized statistical classifiers (e.g., regression function), which may be trained on selected sub-sets of imaging data. For example, specialized statistical classifiers may be applied according to a patient demographic profile, for example, gender (i.e. separate classifiers for males and females) and/or age groups. For example, specialized statistical classifier may be applied according to a scanning protocol, for example, CT scanner (e.g., manufacturer, model, technology type), scanning protocol, and/or radiation dose. Alternatively, the correlation is performed using a common classifier.

Multiple grades may be correlated to a single score. Each of multiple grades may be correlated to a respective score. The lowest score may then be selected. For example, a grade calculated for each vertebra may be correlated to obtain a T-score per vertebra, or a single T-score for all vertebra. Similarly, a lumbar T-score and/or total T-score may be obtained.

Alternatively or additionally, the grade is correlated to one of multiple classification groups. The classification groups may be related to the score. The correlation to the classification group may be performed instead of, or in addition to the correlation to the score.

Optionally, the classification groups are based on pre-defined osteoporosis classification bins: greater than one standard deviation below the mean (−1), between one (−1) and two and a half (−2.5) standard deviations below the mean, and less than two and a half standard deviations below the mean (−2.5). Alternatively or additionally, the classifications are pre-defined diagnostic classification groups: normal, osteoporotic, and osteoporosis. The classification bins may directly correspond to the diagnostic categories: >−1 is normal, −1 to −2.5 is osteoporotic, and <−2.5 is osteoporosis.

Alternatively or additionally, the classification groups are user (or system) defined categories. The classification group bins may be selected, for example, based on a predefined probability threshold, for example, based on a desired sensitivity and/or specificity (or other measures). The classification group bins may be selected to increase the accuracy of the correlation to the specific bin. For example, each bin representing half a standard deviation, or each bin representing a diagnostic classification group: normal, and abnormal.

The correlating is performed by statistical classifier trained on a dataset including, for each patient, a DEXA score calculated from a DEXA scan, and a CT scan generating an imaging dataset used for calculating the grade using the methods described herein. It is noted that multiple classifiers may be trained, for example, based on demographics. For example, T-score classifiers may be trained using different data sets for males and females. For example, Z-score classifiers may be trained using different data sets based on different ages and/or other demographics.

Figure 4:
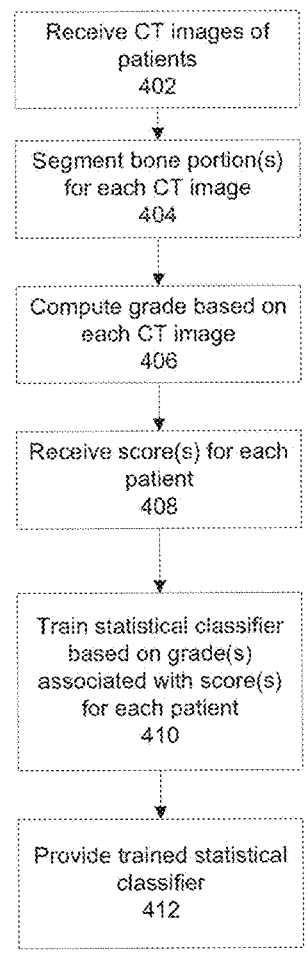
FIG. 4 is a flowchart of a method for creating a trained statistical classifier for use with FIG. 1 and/or FIG. 2, to estimate the DEXA score based on the calculated grade, in accordance with some embodiments of the present invention.

Reference is now made to FIG. 4, which is a flowchart of a method for creating a statistical classifier for use in a process to estimate a DEXA score from CT imaging data, for example, as described with reference to FIG. 1, in accordance with some embodiments of the present invention. Reference is also made back to FIG. 2, in which system 200 trains the statistical classifier, and/or stores the trained statistical classifier. Optionally, processing unit 204 executes code stored in program store 206 to train the classifier. Alternatively or additionally, unit 202 locally stores (or is in communication with) code of a trained classifier 220. Alternatively or additionally, unit 202 obtains the trained classifier from a remote location, such as from a classifier server 222, over a network connection via data interface 218.

System 200 may be divided into two separate systems, such as a first system for training the classifier, and a second system for applying the classifier to acquired medical imaging data. The first system may reside at a central location, such as on a central server, providing the trained classifier to multiple remote locations having the second system, such as radiology workstations. Each radiology workstation receives the trained classifier, and locally applies the classifier to the acquired image data to estimate the score for the scanned patient. Other system architectures may also be used. For example, the classifier training and application of the classifier occur within the same server, such as a server of a health management organization (or other healthcare entity) that houses imaging records for clients. The classifier may be trained on the stored data set, and applied to each new imaging record being added to the data set (i.e., newly acquired images).

At 402, a corpus of training image files is received. The training image files include imaging data of a CT scan of a body image of patient(s) containing designated bone portion(s) (e.g., L1-L4). The CT scan having being performed with settings selected for imaging of non-osteoporosis related pathology.

The corpus of training images may be received by processing unit 204 from image repository 216 (e.g., PACS) via imaging interface 208.

The CT scans may include patients in the prone position and/or the supine position (e.g., a mix of both).

Each patient may be associated with one or more CT scans.

At 404, the bone portion is segmented from the imaging data of each CT scan, for example, as described with reference to block 104 of FIG. 1.

At 406, a grade is computed for the segmented region including the bone portion for each CT scan, for example, as described with reference to block 106 of FIG. 1.

At 408, for each patient having a CT scan, a score calculated based on a DEXA scan is received, for example, a T-score and/or Z-score. The score may be from by unit 202, from a DEXA data server 226 (e.g., a DEXA workstation, or an electronic medical record of the patient storing a DEXA score field), over a communication network (or directly) via data interface 218. Alternatively, the DEXA images are received by unit 202, which calculates the T-score and/or Z-score based on the images.

Optionally, the CT scans and the DEXA scans used for calculating the scores are performed within a time frame of each other representing a statistically similar bone state, for example, no more than about 3 months, or 6 months, or 9 months.

At 408, a statistical classifier is trained based on the computed grade and associated score. The trained statistically classifier is designed to accept the computed grade as an input, and provide a score as output.

Optionally, multiple specialized statistical classifiers (e.g., regression functions) are generated by training on selected sub-sets of training imaging data. For example, specialized statistical classifiers may be trained according to a patient demographic profile, for example, gender (i.e. separate classifiers for males and females) and/or age groups. For example, specialized statistical classifier may be trained according to a scanning protocol, for example, CT scanner (e.g., manufacturer, model, technology type), scanning protocol, and/or radiation dose. Alternatively, a common classifier using the training set.

The statistical classifier may be trained based on suitable training methods, for example, a predictive model, data mining techniques, or other methods. Prediction algorithms may be based on machine learning techniques, for example, artificial neural networks, hierarchical clustering, collaborative filtering, content-based filtering, or other methods.

Optionally, the classifier is trained based on supervised learning. Examples of software modules to train the classifier include: Neural Networks, Support Vector Machines, Decision Trees, Hard/Soft Thresholding, Naive Bayes Classifiers, or any other suitable classification system and/or method. Alternatively or additionally, the classifier is trained based on unsupervised learning methods, for example, k-Nearest Neighbors (KNN) clustering, Gaussian Mixture Model (GMM) parameterization, or other suitable unsupervised methods. Alternatively or additionally, the classifier is trained using regression that provides a transformation from the calculated grade to the score, for example, linear, polynomial, and radial basis function (rbf). The regression method may be deterministic (e.g., minimal square), using random sample consensus (RANSAC), or other learning methods.

Optionally, the classifier is trained using weights. Weights may be assigned to the score according to a diagnosis or other scoring category. The transformation calculation may be weighted regression. For example, different scoring categories may be assigned different weights, for example, to increase the accuracy of diagnosing osteoporosis or osteopenia over a normal diagnosis.

Figure 17:
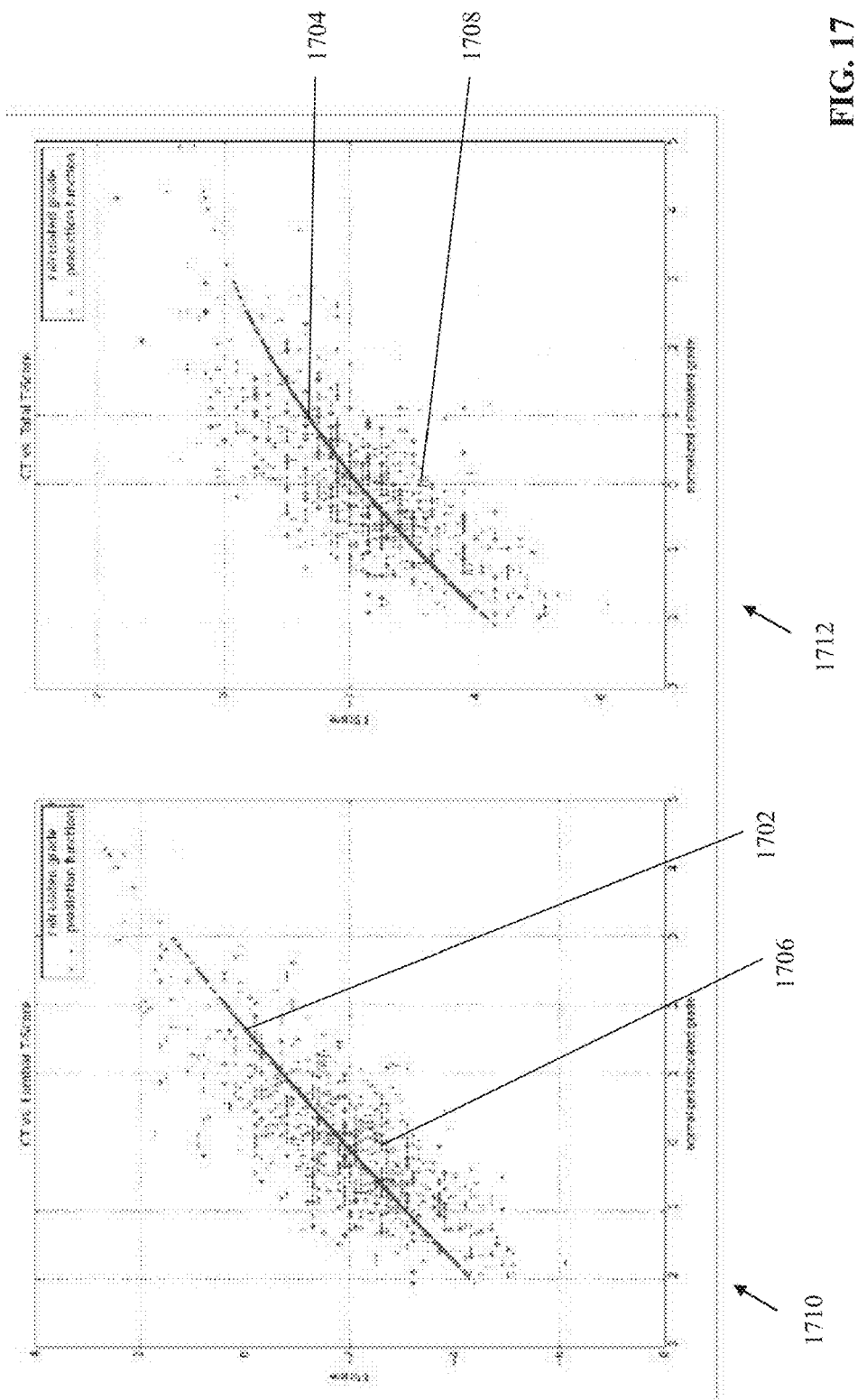
FIG. 17 includes example graphs depicting the creation of a trained classifier, in accordance with some embodiments of the present invention.

Reference is now made to FIG. 17, which includes example graphs depicting the creation of a trained classifier, in the form of a prediction function, in accordance with some embodiments of the present invention. For each graph, a prediction function 1702 1704 is fitted (to a second degree polynomial) on a set of data 1706 1708. Data 1706 1708 is generated by plotting one or more points, for each patient of the training set. Each point includes an x-axis coordinates of the calculated grade (optionally normalized), and a y-axis coordinate of the DEXA T-score. Graph 1710 correlates the (normalized) calculated grade to a lumbar T-score. Graph 1712 correlates the (normalized) calculated grade to a total T-score. The example charts of FIG. 18 illustrate that the error of the generated trained classifier is comparable to the accepted DEXA error rate reported in the literature, of about 5%-8%.

Reference is now made to FIG. 19, which includes tables depicting an increase in accuracy that may be achieved by selecting the categorization bins for the correlated score, in accordance with some embodiments of the present invention. The classifier may be trained to correlate the calculated grade to one of the categorization bins. Table 1902 is a table comparing lumbar T-scores using medically accepted classification category ranges, to actual patient diagnosis, based on about 1000 patients associated with data for training the classifier. The T-score ranges, which are fairly large, may introduce inaccuracy near the borders between the ranges. Table 1904 displays data showing that the accuracy may be increased by using smaller ranges for the bin sizes, for example, about 0.5 (standard deviation).

Figure 20A:
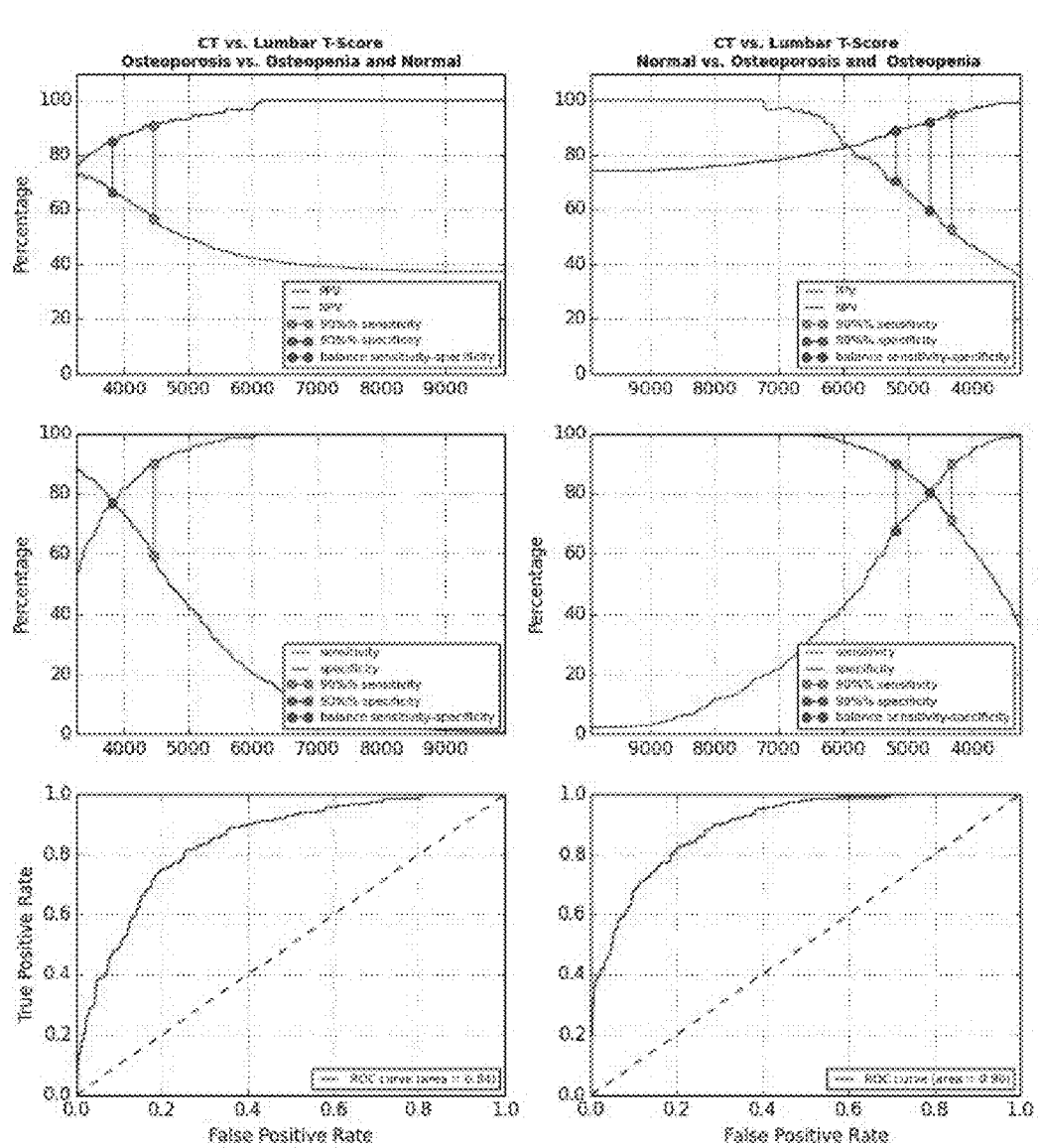
FIGS. 20A-20B include examples of graphs useful for selection of probability thresholds to generate diagnostic categories, for correlation of the grade directly to the diagnostic category, in accordance with some embodiments of the present invention.
Figure 20B:
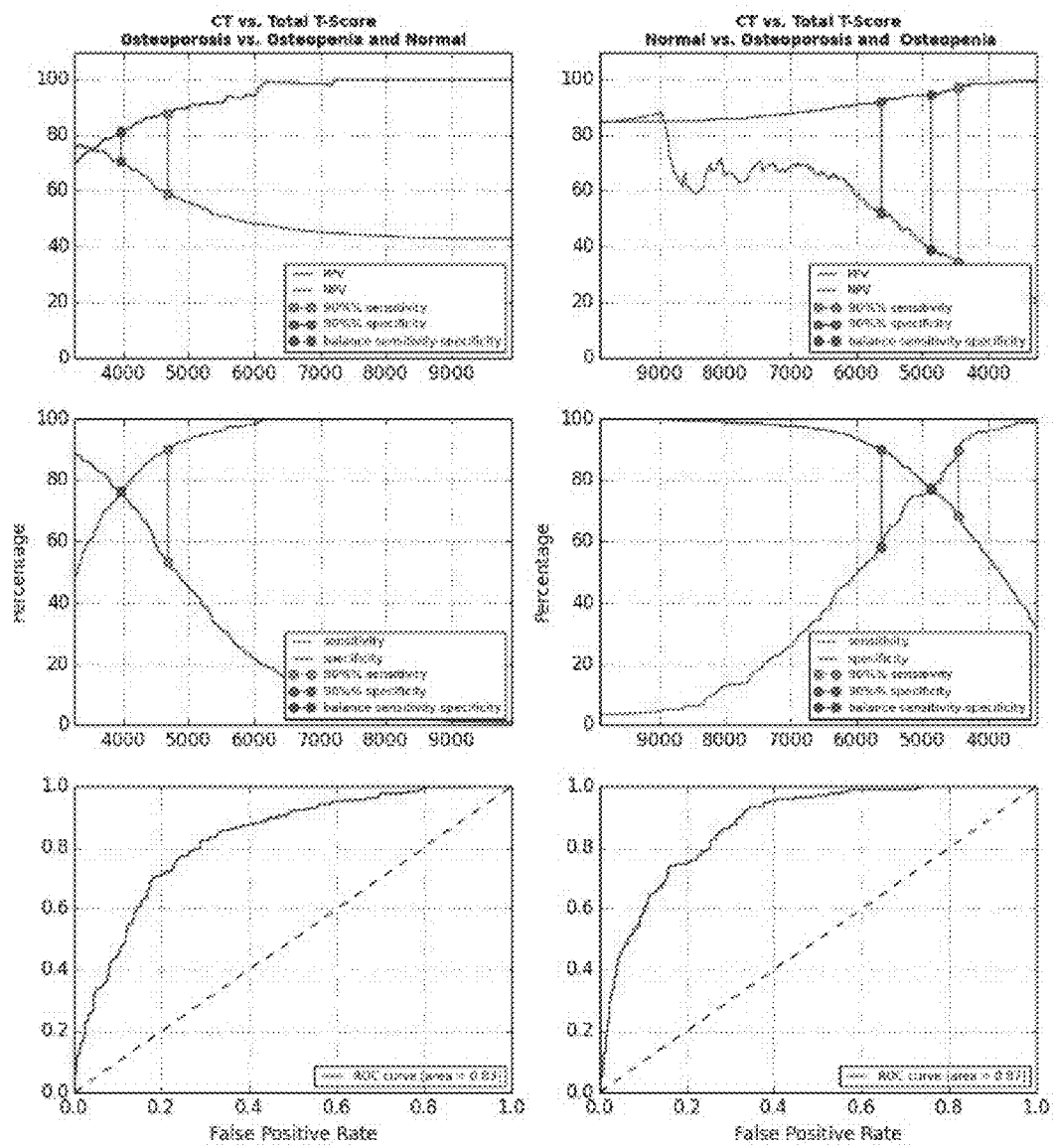

Reference is now made to FIGS. 20A-20B, which include graphs useful for selection of probability thresholds to generate diagnostic categories, for correlation of the grade directly to the diagnostic category (instead of to the T-score or Z-score), in accordance with some embodiments of the present invention. The classifier may be trained to classify the grade to the respective diagnostic category, to achieve the desired probability threshold, for example, to obtain a desired sensitivity, specificity, positive predictive value, and/or negative predictive value. The probability thresholds may be manually selected by the use, or automatically assigned by the system, for example, based on an optimal trade-off between different thresholds. The diagnostic categories may include two categories, for example, normal and abnormal (i.e., osteoporosis and/or osteopenia), osteoporosis and other (i.e., normal and/or osteopenia). Different probability thresholds for the diagnostic categories may be selected for the lumbar T-score and the total T-score (as shown by the different charts).

Referring now back to FIG. 4, at 410, the trained statistical classifier is provided, for example, locally stored as trained classifier 220, or uploaded to a central server 228.

Referring now back to FIG. 1, at 109, the patient is selected according to a requirement of the score. Optionally, when the method of FIG. 1, is applied to a corpus of CT image files acquired from multiple patients (e.g., stored in a PACS server and/or stored in association with patient medical records), a group from the corpus is selected according to the requirement of the score.

Optionally, the requirement is a designation of one or more of the diagnostic classification group (e.g., as described with reference to block 108), for example, abnormal, osteoporosis, and/or osteopenia. Alternatively or additionally, the requirement is a designation of one or more of the classification bins, for example, the bins of: below −2.5, and/or −2.5 to −1, or other bins. Alternatively or additionally, the requirement is a threshold value or a range of values of the DEXA score (e.g., T-score and/or Z-score), for example, below −2.5, below −1, between −2.5 and −1, or other values.

At 110, the correlated score(s) and/or an indication of the selected patient(s) (i.e., the group from the corpus) is provided. The correlated score and/or indication may be outputted via output interface 210. The correlated score may be presented on user interface 212 (e.g., display), stored in a storage device, undergo additional processing, and/or transmitted to a server 228.

Optionally, a presentation that includes the correlated score, optionally the T-score and/or Z-score is generated. The presentation may include the calculated grade use to correlate to the grade. The grade and/or score(s) may be presented for each (or sub-sets of) the segmented bones (e.g., vertebra).

Optionally, the presentation includes the processed data serving as the basis for calculation of the grade, for example, as described with reference to image 1612 of FIG. 16F.

Optionally, the presentation includes a sagittal and/or a coronal slice of the CT including the bone portion. The identified line representing the lower limit of the lung of the patient and/or the identified line representing the hip (or L5) of the patient may be marked on the CT slice.

Figure 21:
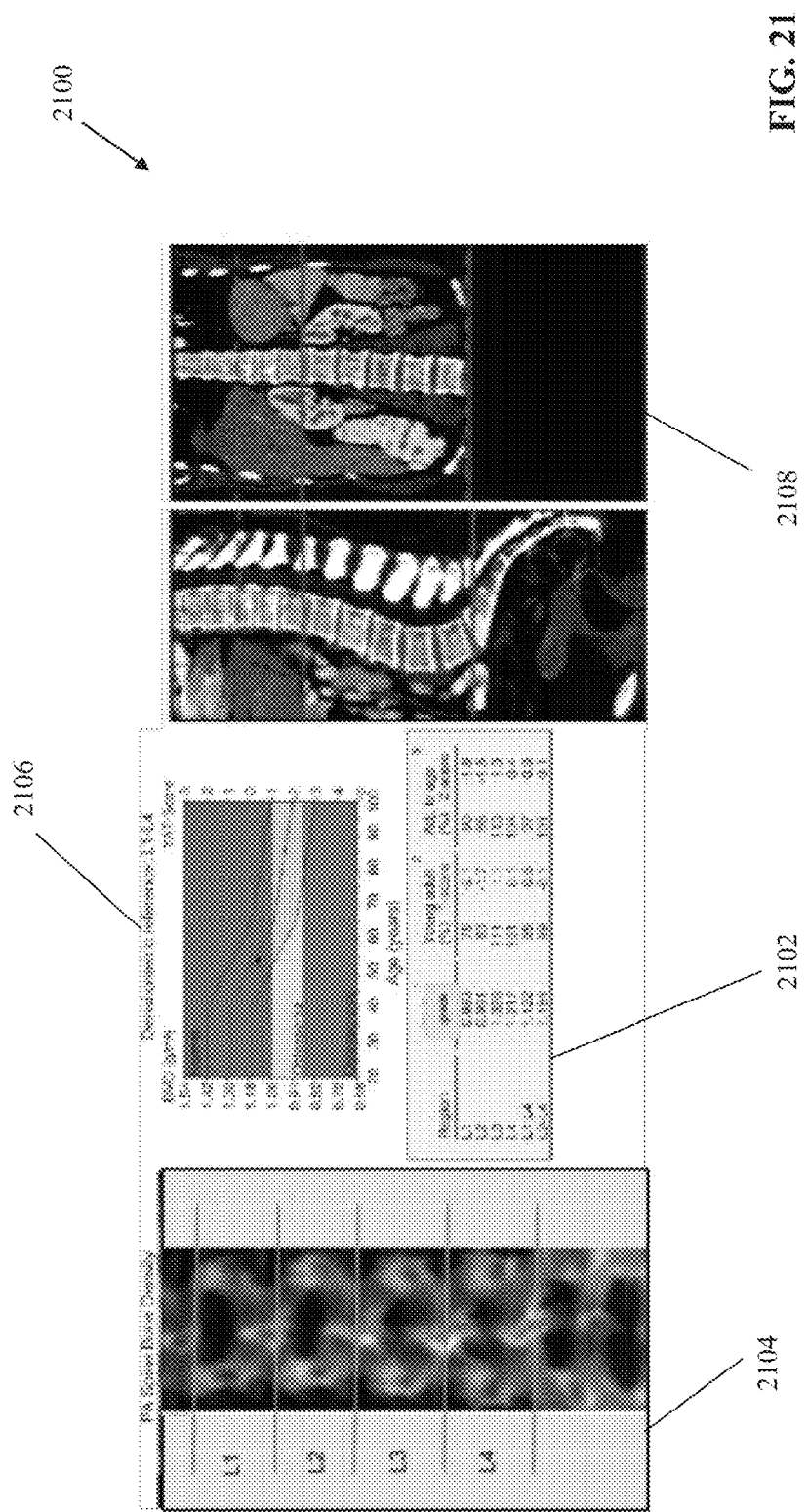
FIG. 21 is an exemplary presentation including the estimated score, in accordance with some embodiments of the present invention.

Reference is now made to FIG. 21, which is an exemplary presentation 2100 including the estimated score, in accordance with some embodiments of the present invention. Presentation 2100 includes a region 2102 displaying, optionally as a table, the grade and correlated T-scores and/or Z-scores. The grade and scores may be presented for each identified bone (e.g., each of L1-L4), for all bones (e.g., L1-L4), or for a selected subset of bones (e.g., L2-L4).

Figure 16:
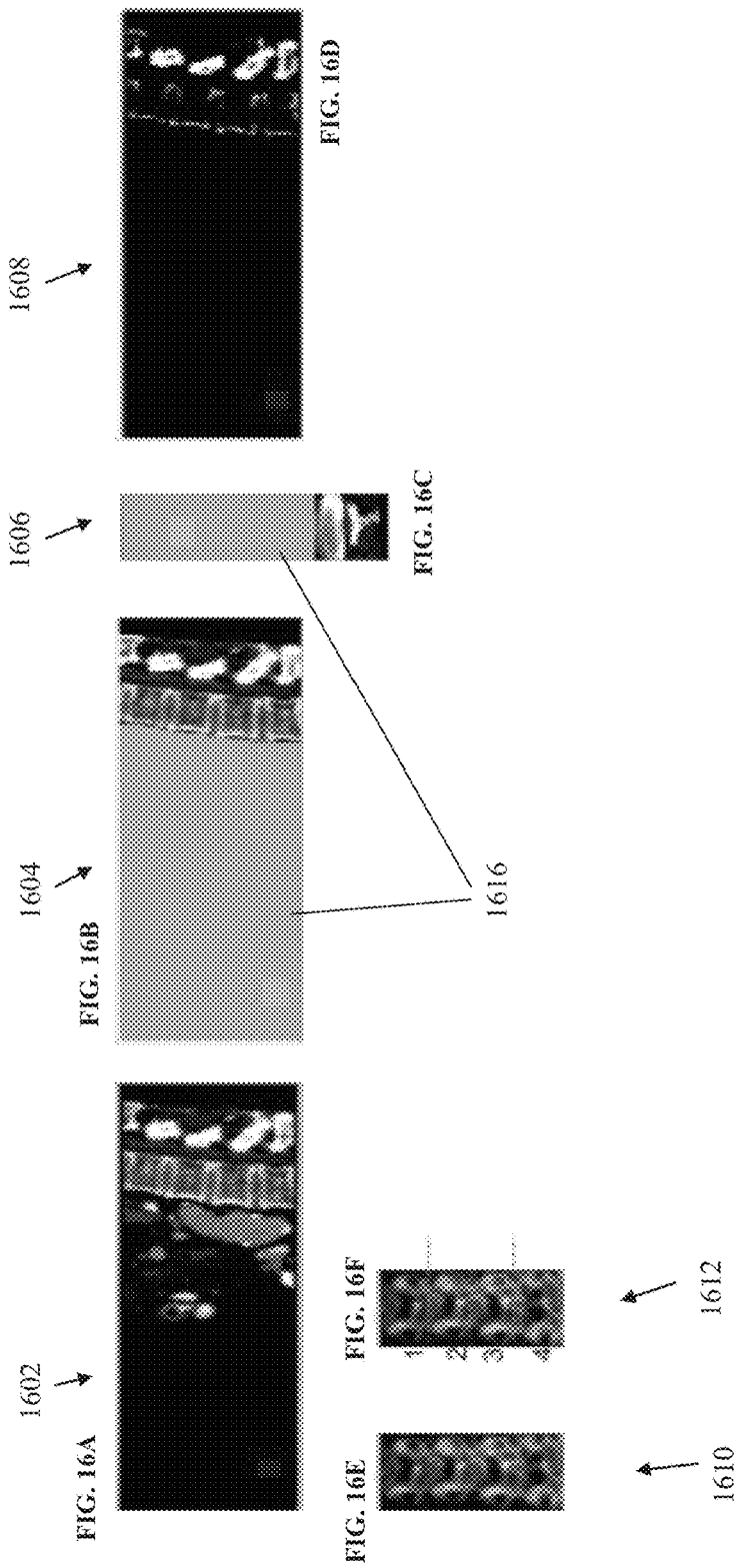
FIGS. 16A-16F include images depicting calculation of the grade, in accordance with some embodiments of the present invention.

Presentation 2100 may include an image 2104 of the processed data used for calculation of the grade, which may include the identified bones, and may include border lines separating between the bones (e.g., as described herein and/or with reference to image 1612 of FIG. 16F).

Presentation 2100 may include reference information 2106, relating the T-scores with absolute bone mineral density values, and with diagnostic categories, for different ages.

Presentation 2100 may include includes a sagittal and/or a coronal slice of the CT including the bone portion, optionally with markings of the lower limit of the lung of the patient and/or the hip (e.g., as described herein, and/or with reference to FIG. 14).

It is noted that the systems and/or methods described herein may be combined with the systems and/or methods described in Provisional Patent Application No. 62/026,730 filed Jul. 21, 2014, incorporated herein by reference in its entirety, which teaches systems and/or methods for predicting risk of osteoporotic fracture. For example, the received imaging data (e.g., CT image) may be further analyzed to predict the risk of osteoporotic fracture in the patient, in addition to the estimated T-score. In another example, the system may also train classifiers, using images derived from the same corpus of images, to also predict risk of fracture. The combined systems and/or methods may provide multiple osteoporosis related data from the same CT image acquired for non-osteoporosis pathology.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant imaging modalities and scoring systems will be developed and the scope of the terms DEXA, DXA, CT, T-score, and Z-score are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computerized method for estimating at least one score representing a relation to bone mineral density (BMD) values in a population from three dimensional (3D) computed tomography (CT) imaging data, comprising:

receiving 3D imaging data of a CT scan of a body of a patient containing at least a 3D bone portion;

segmenting the 3D bone portion from the 3D imaging data of the CT scan;

computing at least one grade for the 3D bone portion based on pixel associated values from the 3D bone portion;

correlating the at least one grade of the 3D bone portion with the at least one score representing the relation to BMD values in the population, wherein the at least one grade for the 3D bone portion is computed from a calculation of sub-grades performed for each one or a set of pixels having at least one of a common medial-lateral axial coordinate and a common cranial-caudal axial coordinate along a dorsal-ventral axis of a volume representation of the 3D imaging data of the CT scan; and presenting the at least one score correlated to the least one grade on a presentation unit for diagnosis of at least one of abnormal BMD, osteoporosis, and osteopenia.

2. The method of claim 1, wherein the grade is computed from sub-grades calculated for each of the bone portions comprising at least one of: a femur, and vertebral bodies of at least one of L1, L2, L3, and L4 vertebrae.

3. The method of claim 2, further comprising presenting the values of the sub-grades computed according to at least one of: a trabecular portion and a cortical portion of the respective vertebral body.

4. The method of claim 3, further comprising correlating each sub-grade computed according to at least one of: a trabecular portion and a cortical portion of the respective vertebral body, with at least one score representing a relation to bone density values in the population.

5. The method of claim 3, further comprising computing a predicted risk of osteoporotic fracture at a future time frame for each of the bone portions according to at least one of: the values of the sub-grades and at least one score representing a relation to bone density values in a population correlated to the values of the sub-grades.

6. The method of claim 1, wherein the grade is computed by calculation of an average pixel associated value for pixel associated values above a predefined threshold selected from about 150-300 Hounsfield Units (HU), the pixels having a common x,z-coordinate, and along a y-axis of a volume representation of the imaging data.

7. The method of claim 1, wherein the grade is computed based on at least one member of the group consisting of:

minimal grade of sub-grades computed for each vertebra of a plurality of vertebrae, average grade of sub-grades computed for a plurality of vertebrae, average grade of sub-grades computed for a plurality of defined sections each including portions of a plurality of vertebrae, and grade computation for a single predefined vertebra.

8. The method of claim 1, further comprising inverting pixel coordinates of the imaging data according to a predefined common patient position when the predefined common patient position is different than an identified position of the patient.

9. The method of claim 1, wherein the segmented bone portion excludes contrast agent having pixel associated values representing bone.

10. The method of claim 1, wherein the correlating comprises at least one of: selecting a grade from a plurality of sub-grades to correlate with a single score, and correlating each of a plurality of sub-grades with a respective sub-score and selecting the lowest sub-score as the score.

11. The method of claim 1, wherein the correlating is performed by a statistical classifier trained on a dataset including, for each patient, a BMD value, and a CT scan generating an imaging dataset used for calculating the grade.

12. The method of claim 1, wherein segmenting the bone portion from the imaging data comprises: identifying a z-coordinate limitation of a region of interest (Z-ROI) including the L1-L4 lumbar vertebrae from the imaging data, and per z-coordinate slice identifying an x-coordinate limitation of the respective vertebrae (X-ROI).

13. The method of claim 1, further comprising:
counting a number of pixels representing lung tissue for each axial slice of a volume generated from the imaging data;
designating z-coordinates according to the largest identified decrease in the number of lung pixels between sequential axial slices, wherein the designated z-coordinates represent an approximate location of the T12 vertebrae; and
wherein segmenting comprises segmenting at least one of the L1-L4 vertebrae according to the designated z-coordinates.

14. The method of claim 1, further comprising:
analyzing a sagittal section of the imaging data to identify a border of a back of the patient; and
wherein segmenting comprises segmenting at least one of the L1-L4 vertebrae according to the identified border of the back of the patient.

15. The method of claim 14, wherein the analyzing is performed using an image window size selected to exclude ribs to identify a first of the border, and further comprising:
analyzing the sagittal section of the image data using a second window size selected to include ribs to identify a second border of the back of the patient;
comparing proximity of the coordinates of the first border to the second border;
identifying a position of the patient relative to a scan table according to the proximity of the coordinates; and
inverting pixel coordinates of the imaging data according to a predefined common patient position when the predefined common patient position is different than an identified position of the patient.

16. The method of claim 14, wherein segmenting comprises generating a binary map of a region large enough to include vertebra and connected rib portions while excluding other nearby tissues from the identified border according to a first pixel associated value assigned to pixels in the region above a pixel threshold, and a second pixel associated value assigned to pixels in the region below the pixel threshold, wherein the binary map is generated in a coronal view.

17. The method of claim 1, further comprising:
selecting a largest connected component of the imaging data that crosses a z-coordinate defining an end of a lung of the patient; and
identifying a central line of the largest connected component;
identifying side boundaries of the largest connected component;
wherein the largest connected component is a binary map having values representing bone or other nearby tissue;
and wherein segmenting comprises segmenting according to the largest connected component by identifying the L1-L4 on the imaging data by correlating the largest connected components to the imaging data to identify a T12 vertebrate when a lowest rib is connected and an L5 vertebrae according to a location where the width of the largest connected component increases representing a hip of the patient.

18. The method of claim 1, wherein segmenting is performed on a sagittal section defined within a region of the imaging data designated below an identified lower limit of a lung of the patient and a border of a back of the patient, a border between a vertebral column of the patient and other organs in near proximity, and a border between a spinal cord and the vertebral column, such that the identified vertebral column includes vertebral bodies and excludes vertebral pedicles and processes.

19. The method of claim 1, wherein segmenting comprises transforming identified vertebral bodies to a vertical alignment according to calculated gradients between each vertebral body and the spinal column, identifying borders of at least one of the L1, L2, L3, and L4 vertebral bodies on the vertical alignment according to identified vertical lines, and marking the identified vertebral bodies on the imaging data according to a mapping from the vertical alignment to the imaging data.

20. The method of claim 1, wherein segmenting comprises identifying an approximate region of interest (ROI) including an un-segmented component of the bone portion and another connected bone other than the bone portion.

21. The method of claim 1, wherein segmenting comprises:
identifying an insufficient amount of contrast agent to affect the grade calculation; and
excluding a scanning bed from the imaging data by identifying a single component of the patient's body, and selecting the single component.

22. The method of claim 1, wherein the at least one score represents the relation to bone density values in a population selected from the group consisting of: a healthy young population, and a demographically similar population.

23. A system for estimating a at least one score representing a relation to bone mineral density (BMD) values in a population from 3D CT imaging data, comprising:
an imaging interface for receiving 3D imaging data of a CT scan of a body of a patient containing at least a 3D bone portion;
an output interface for communicating with a user interface;
a code stored in a non-transitory computer-readable medium; and
a processor coupled to the imaging interface, the output interface, and the non-transitory computer-readable medium for implementing the stored code, the code comprising:

code to receive the 3D imaging data;
code to segment the 3D bone portion from the 3D imaging data of the CT scan;
code to compute at least one grade for the 3D bone portion based on pixel associated values from the 3D bone portion;
code to correlate the at least one grade of the 3D bone portion with the at least one score representing the relation to BMD values in the population; and
code to provide the at least one score correlated to the least one grade to the output interface for presentation on the user interface for diagnosis of at least one of abnormal BMD, osteoporosis, and osteopenia;
wherein the at least one grade for the 3D bone portion is computed from a calculation of sub-grades performed for each one or a set of pixels having at least one of a common medial-lateral axial coordinate and a common cranial-caudal axial coordinate along a dorsal-ventral axis of a volume representation of the 3D imaging data of the CT scan.

24. A computer program product for estimating at least one score representing a relation to bone mineral density (BMD) values in a population from three dimensional (3D) computed tomography (CT) imaging data, comprising:
a non-transitory memory having stored thereon a code for execution by at least one hardware processor, the code comprising instructions for:
receiving 3D imaging data of a CT scan of a body of a patient containing at least a 3D bone portion;
segmenting the 3D bone portion from the 3D imaging data of the CT scan;
computing at least one grade for the 3D bone portion based on pixel associated values from the 3D bone portion;
correlating the at least one grade of the 3D bone portion with the at least one score representing the relation to BMD values in the population,
wherein the at least one grade for the 3D bone portion is computed from a calculation of sub-grades performed for each one or a set of pixels having at least one of a common medial-lateral axial coordinate and a common cranial-caudal axial coordinate along a dorsal-ventral axis of a volume representation of the 3D imaging data of the CT scan; and
presenting the at least one score correlated to the least one grade on a presentation unit for diagnosis of at least one of abnormal BMD, osteoporosis, and osteopenia.

* * * * *